(12) United States Patent
Mairesse et al.

(10) Patent No.: US 12,351,793 B2
(45) Date of Patent: Jul. 8, 2025

(54) SYSTEM AND METHOD FOR THE PRODUCTION OF BIOMOLECULES

(71) Applicant: UNIVERCELLS TECHNOLOGIES S.A., Nivelles (BE)

(72) Inventors: Bastien Mairesse, Uccle (BE); Laetitia De Viron, Ecaussinnes (BE); Alex Chatel, Brussels (BE)

(73) Assignee: UNIVERCELLS TECHNOLOGIES S.A., Nivelles (BE)

( * ) Notice: Subject to any disclaimer, the term of this patent is extended or adjusted under 35 U.S.C. 154(b) by 891 days.

(21) Appl. No.: 17/263,402

(22) PCT Filed: Jun. 27, 2019

(86) PCT No.: PCT/EP2019/067263
§ 371 (c)(1),
(2) Date: Jan. 26, 2021

(87) PCT Pub. No.: WO2020/020569
PCT Pub. Date: Jan. 30, 2020

(65) Prior Publication Data
US 2021/0155892 A1  May 27, 2021

Related U.S. Application Data

(60) Provisional application No. 62/795,820, filed on Jan. 23, 2019, provisional application No. 62/711,070, filed on Jul. 27, 2018.

(30) Foreign Application Priority Data

Sep. 27, 2018 (WO) ................. PCT/EP2018/076354

(51) Int. Cl.
*C12M 1/00* (2006.01)
*C12M 1/36* (2006.01)
*C12M 3/00* (2006.01)

(52) U.S. Cl.
CPC ............ *C12M 47/10* (2013.01); *C12M 29/04* (2013.01); *C12M 41/48* (2013.01)

(58) Field of Classification Search
CPC .............................. C12M 29/18; C12M 47/10
See application file for complete search history.

(56) References Cited

U.S. PATENT DOCUMENTS

| 5,501,971 A | 3/1996 | Freedman |
| 2011/0003380 A1* | 1/2011 | Miltenyi ............... B03C 1/0332 494/67 |

(Continued)

FOREIGN PATENT DOCUMENTS

| EP | 0995483 A1 * | 4/2000 |
| EP | 2208534 A1 | 7/2010 |

(Continued)

OTHER PUBLICATIONS

Peng Shuangqing; "Key Technologies for Drug Safety Evaluation"; Military Medical Science Press, 2013.

(Continued)

*Primary Examiner* — Nathan A Bowers
(74) *Attorney, Agent, or Firm* — Dickinson Wright PLLC; Andrew D. Dorisio

(57) ABSTRACT

The current disclosure concerns a system for producing biomolecules comprising a docking station (30), said docking station encompasses: —a bioreactor (1); —a concentrator (2) fluidly linked to the bioreactor; —an intermediate vessel (4), positioned between said bioreactor (1) and concentrator (2), wherein said intermediate vessel (4) and concentrator (2) are connected by a retentate conduit (303), allowing recirculating of liquid from an output of the concentrator to an input of said intermediate vessel and—a controller, integrated in said docking station (30), which is able to control the biomolecule process.

19 Claims, 25 Drawing Sheets

(56) References Cited

U.S. PATENT DOCUMENTS

| | | | | |
|---|---|---|---|---|
| 2011/0263021 A1* | 10/2011 | Stobbe | ................ | F04B 43/0736 |
| | | | | 435/243 |
| 2013/0115588 A1 | 5/2013 | Davis et al. | | |
| 2016/0195081 A1 | 7/2016 | Stobbe | | |
| 2016/0222337 A1 | 8/2016 | Serway | | |
| 2018/0282682 A1* | 10/2018 | Pebay | .................... | C12M 41/48 |

FOREIGN PATENT DOCUMENTS

| | | | |
|---|---|---|---|
| JP | 2003512594 A | 4/2003 |
| JP | 2013526269 A | 6/2013 |
| JP | 2015526094 A | 9/2015 |
| WO | 2006005305 A2 | 1/2006 |
| WO | 2011130617 A2 | 10/2011 |
| WO | 2013144091 A1 | 10/2013 |
| WO | 2014051503 A1 | 4/2014 |
| WO | 2015118148 A1 | 8/2015 |
| WO | 2018087235 A1 | 5/2018 |
| WO | 2019122239 A1 | 6/2019 |

OTHER PUBLICATIONS

Zhang Genabo; "Industrial Automation Instrumentation and Process Control"; Northwestern Polytechincal University Press, 2008.
Huo Nairui; Microbial Biology, China Agricultural University Press, 2018, China.

* cited by examiner

SYSTEM AND METHOD FOR THE PRODUCTION OF BIOMOLECULES

TECHNICAL FIELD

The invention pertains to the technical field of the production of biomolecules such as viral vaccines or antibodies and describes a system and method thereto.

BACKGROUND

Due to the vast number of diseases caused by pathogenic bacteria and viruses, there remains a large demand in the field to produce biomolecules such as antibodies and viruses efficiently.

The traditional methods of purifying biomolecules, especially viruses, from cultured cells are tedious and time consuming, rendering the cost of biomolecule production too high. In order to obtain products suitable for clinical administration, fast and efficient methods of producing biomolecules such as virus or viral proteins in cultured cells are needed.

In addition, there is a need for systems that are concise and require a minimum of space and which can be easily transported, for instance to be placed on a bench or in a flow.

The present disclosure aims to resolve at least some of the problems mentioned above. The present disclosure provides a system adapted for the purification of biomolecules with a minimum of biomolecule loss and assurance of high biomolecule quality in a restricted amount of space. Second, it is also the aim to provide a methodology with a limited amount of operational steps that still provides a high yield of biomolecule, with a significant reduction of operation expenses (OPEX) and a high level of containment.

SUMMARY

The present disclosure provides a system for producing biomolecules according to claim 1. More in particular, the disclosure provides a system for producing biomolecules comprising a docking station, said docking station encompasses:
  a bioreactor including a chamber suitable for receiving a liquid comprising a target biomolecule;
  a concentrator fluidly linked to the bioreactor;
  an intermediate vessel, positioned between said bioreactor and concentrator, wherein said intermediate vessel and concentrator are connected by a retentate conduit, allowing recirculating of liquid from an output of the concentrator to an input of said intermediate vessel and
  a controller, integrated in said docking station, which is able to control the biomolecule process.

The system is low-footprint, flexible and enables rapid process development as well as the production of batches for clinical applications. The modular structure and linear scalability ensures a smooth transition from R&D to clinical stages as well as full-scale industrial production. The system is designed to be used within either a laminar flow or biosafety cabinet.

In a second aspect, the present disclosure provides a method according to claim 18. More in particular the present disclosure provides a method for producing biomolecules, wherein said biomolecules are produced in a bioreactor comprising a liquid comprising cells, said method comprises a concentration step, wherein output from said bioreactor is concentrated in a concentrator and wherein output from said concentrator is recirculated to said bioreactor or to an intermediate vessel positioned between said concentrator and said bioreactor.

Definitions

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

As used herein, the following terms have the following meanings:

"A", "an", and "the" as used herein refers to both singular and plural referents unless the context clearly dictates otherwise. By way of example, "a compartment" refers to one or more than one compartment.

"About" as used herein referring to a measurable value such as a parameter, an amount, a temporal duration, and the like, is meant to encompass variations of +/−20% or less, preferably +/−10% or less, more preferably +/−5% or less, even more preferably +/−1% or less, and still more preferably +/−0.1% or less of and from the specified value, in so far such variations are appropriate to perform in the disclosed invention. However, it is to be understood that the value to which the modifier "about" refers is itself also specifically disclosed.

"Comprise", "comprising", and "comprises" and "comprised of" as used herein are synonymous with "include", "including", "includes" or "contain", "containing", "contains" and are inclusive or open-ended terms that specifies the presence of what follows e.g. component and do not exclude or preclude the presence of additional, non-recited components, features, element, members, steps, known in the art or disclosed therein.

The recitation of numerical ranges by endpoints includes all numbers and fractions subsumed within that range, as well as the recited endpoints.

The expression "% by weight", "weight percent", "% wt" or "wt %", here and throughout the description unless otherwise defined, refers to the relative weight of the respective component based on the overall weight of the formulation.

"Biomolecule" refers to any biological material of interest that is produced in a bioreactor. Biomolecules include, for example, viruses, virus-like particles, viral products, proteins such as antibodies, carbohydrates, lipids, nucleic acids, metabolites and peptides.

"Antibody" refers to any immunoglobulin molecule, antigen-binding immunoglobulin fragment or immunoglobulin fusion protein, monoclonal or polyclonal, derived from human or other animal cell lines, including natural or genetically modified forms such as humanized, human, chimeric, synthetic, recombinant, hybrid, mutated, grafted, and in vitro generated antibodies. Commonly known natural immunoglobulin antibodies include IgA (dimeric), IgG, IgE, IgG and IgM (pentameric).

"Virus" or "virion" refers to an ultramicroscopic (roughly 20 to 300 nm in diameter), infectious agent that replicates only within the cells of living hosts, mainly bacteria, plants, and animals: composed of an RNA or DNA core, a protein coat, and, in more complex types, a surrounding envelope.

"Bioreactor" refers to any device or system that supports a biologically active environment, for example for cultivation of cells or organisms for production of a biological product. This would include cell stacks, roller bottles, shakes, flasks, stirred tank suspension bioreactors, high cell density fixed-bed perfusion bioreactors, etc.

"Purification" refers to the substantial reduction of the concentration of one or more target impurities or contaminants relative to the concentration of a target biomolecule.

"Tangential flow filtration (TEE)" refers to a method of membrane filtration in which fluid is forced through a space bounded by one or more porous membranes, where molecules small enough to pass through the pores are eliminated in the filtrate or "permeate", and molecules large enough to be rejected by the pores remain in the "retentate". The name tangential flow particularly refers to the fact that the direction of fluid flow is roughly parallel to the membrane, as opposed to so-called dead-end filtration where flow is roughly perpendicular to the membrane.

As used herein, "viral infection" refers to the entry of a virus into a cell and the subsequent replication of the virus in the cell.

"Cell culture harvest", "culture harvest" and "harvest" are used as synonyms and refer to the unclarified cell culture obtained from culturing cells in a bioreactor. The cultured cells or the grown cells also are referred to as host cells.

"Serial, in-line" means that devices or units are connected such that the outflow of one unit or device is directly fed into a subsequent unit or device, without intermediate storage.

"Isolator" or "cabinet" are used herein as synonyms and refer to a ventilated laboratory workspace for safely working with biological materials. "Isolator" includes enclosed isolators for containment of materials contaminated with (or potentially contaminated with) pathogens, enclosed biosafety cabinets for containment of materials contaminated with (or potentially contaminated with) pathogens and for protection of the product (e.g. purified target biomolecule) from contamination and laminar flow cabinets for protection of the product (e.g. a purified target biomolecule) from contamination.

BRIEF DESCRIPTION OF FIGURES

FIGS. 4, 4A, and 4B illustrate a possible environment of use of the bioreactor of FIG. 3.

FIGS. 31 and 32 are graphs illustrating testing of the bioreactor.

FIGS. 33 and 34 are graphs illustrating testing of the bioreactor to assess cell density of structured fixed beds in a stacked configuration.

DETAILED DESCRIPTION

Figure 1:
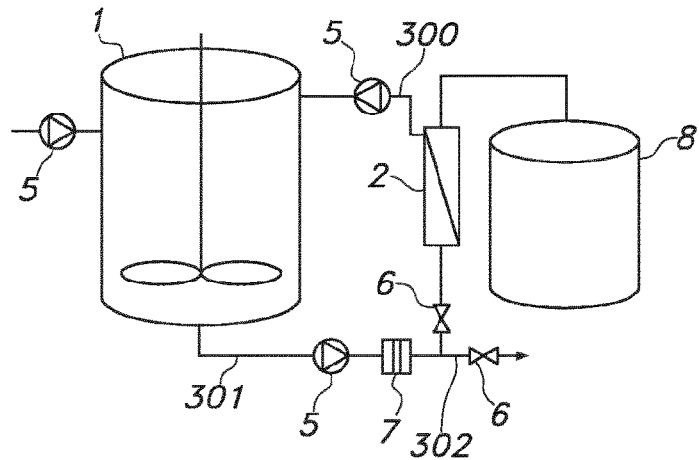
FIG. 1 shows a schematic overview of a system for producing biomolecules according to an embodiment of the disclosure.

The present invention concerns a system as well as a method for the purification of biomolecules such as proteins or viruses. The system is low-footprint, has a high surface area and is linear scalable and as such enables rapid process development as well as the production of batches for clinical applications. The modular structure and linear scalability of the system ensures a smooth transition from R&D to clinical stages as well as full-scale industrial production. The system is designed to be used within either a laminar flow or biosafety cabinet.

In a first aspect, the disclosure provides a system for producing biomolecules comprising a docking station, said docking station encompasses:
    a bioreactor including a chamber suitable for receiving a liquid comprising a target biomolecule;
    a concentrator fluidly linked to the bioreactor;
    an intermediate vessel, positioned between said bioreactor and concentrator, wherein said intermediate vessel and concentrator are connected by a retentate conduit, allowing recirculating of liquid from an output of the concentrator to an input of said intermediate vessel and
    a controller, integrated in said docking station, which is able to control the biomolecule process.

In a further aspect, the disclosure provides a system for producing biomolecules comprising a bioreactor including a chamber suitable for receiving a liquid comprising a target biomolecule, a concentrator, and an intermediate vessel comprising the cell culture harvest comprising the target biomolecule in a concentration higher than the target biomolecule in the bioreactor.

The benchtop system of the current disclosure is designed such that it may be used within either a laminar flow or biosafety cabinet and features a touchscreen for quick-access function (e.g. pump priming, visual representation of live status and monitoring parameters) as well as docking slots for base, inoculum and a vessel for concentrated product is being used. The controller housing can be made of any suitable material but is preferably manufactured out of stainless steel and is designed to enable user-friendly cleaning. In some embodiments the footprint occupied by the controller housing is less than about 5000 cm$^2$.

This system integrates intensification technologies, thereby drastically reducing the size of each compartment and hence creating a low footprint production and purification system. The production and purification of the biomolecule can be performed as a continuous and automated process based on this system: from cell culture to final product purification minimizing human intervention. The process intensification and integration enable the containment of all compartments into an isolator ensuring the safety of process operators and the environment. The system has a small footprint. In some embodiments, the footprint of the system is less than about 50 m$^2$, 40 m$^2$, 30 m$^2$, 20 m$^2$, 10 m$^2$, 5 m$^2$, or less. In some embodiments, the footprint of the system is from about 5 m$^2$ to 10 m$^2$, 5 m$^2$ to 20 m$^2$, 5 to 30 m$^2$, 5 to 40 m$^2$, 5 to 50 m$^2$. In an example, the footprint is less than 10 m$^2$. For example, a 7 m$^2$ system can produce at least 0.5 million doses of a viral vaccine per batch, or about 10$^7$ doses per year. As a consequence, this autonomous process has a dramatic impact on the economics of biomolecule production by significantly reducing the cost of goods as well as capital expenditures.

The system for producing biomolecules of the present disclosure allows down-scaling of the infrastructure required for biomolecule production on an industrial level, thereby also allowing to reduce the amount of consumables. The system reduces the amount of consumables used by greater than or equal to about 10%, 20%, 30%, 40%, 50%, 60%, 70%, 80%, 90%, or more. The system reduces the amount of consumables used from about 10% to 20%, 10% to 30%, 10% to 40%, 10% to 50%, 10% to 60%, 10% to 70%, 10% to 80%, 10% to 90%. The system further allows to purify a biomolecule in a safe, efficient and cost-effective manner.

The system of the disclosure allows rapid production and purification of biomolecules such as recombinant proteins, viruses or viral products using significantly smaller equipment as compared to systems of the prior art. In addition, high yield of the biomolecule is obtained using the system, thereby reducing the costs of the final product. The recovery of the target biomolecule may be greater than or equal to 65%, 70%, 75%, 80%, 85%, 90%. This eventually results in a lower investment and production cost, which is a considerable advantage.

The system comprises at least one bioreactor for cell growth and/or for cells products production. In an embodiment the bioreactor is a single-use bioreactor. In another embodiment the bioreactor is autoclavable. The system is designed to be used for the growth of adherent cells, as well as non-adherent cells. In an embodiment the bioreactor is a batch bioreactor. In another embodiment the bioreactor is a perfusion bioreactor. In a perfusion bioreactor equivalent volumes of media are simultaneously added to and removed from the bioreactor, while the cells are retained in the bioreactor. This provides a steady source of fresh nutrients and constant removal of cell (waste) products. Perfusion allows to attain much higher cell density and thus a higher volumetric productivity than conventional bioreactors. In addition, the perfusion bioreactor allows for secreted products to be continuously harvested during the process of removing media. Preferably, the bioreactor is a fixed-bed perfusion bioreactor. A fixed-bed configuration allows for a higher cell density growth to be achieved in the system and which provides for use of a bioreactor which is smaller than conventional bioreactors. Said bioreactor easily allows for a cell density of at least 50 million cells/ml to be achieved. Accordingly, the system makes use of a bioreactor which is smaller than conventional bioreactors, without compromising the high density cell culture capabilities of the bioreactor. Therefore, incorporation of a bioreactor as described allows for a reduction in terms of the space required for the system. Owing to the intensification of cell culture using this type of bioreactor the system is thus provided with a high cell density bioreactor that is small enough to be placed in the docking station. In another embodiment the system is equipped with a bioreactor suitable to be operated both in batch mode and in perfusion mode. This can be advantageous as the bioreactor in the system can be adapted to specific steps in the production and purification process e.g. the bioreactor can be operated in batch mode during inoculation, and in perfusion mode during cell growth.

In some embodiments, a bioreactor disclosed herein allows for high density cell growth. For example, density of at least 2 million cells/ml, at least 5 million cells/ml, at least 10 million cells/ml, at least 20 million cells/ml, at least 40 million cells/ml, at least 60 million cells/ml, or at least 100 million cells/ml. In some embodiments, the density can reach 300, 250 or 200 million cells/ml. In some embodiments, the bioreactor disclosed herein can have a total volume of at least 1 L, at least 10 L, at least 30 L, at least 40 L, or at least 50 L. By bioreactor total volume reference can be made to the total liquid volume that can be introduced in the bioreactor, which will then be full. In some embodiments, the effective surface area for cell growth ranges from 1 to 50 m$^2$, or from 5 to 40 m$^2$ or from 7.5 to 30 m$^2$ In an embodiment, the system is provided with a bioreactor as described in PCT/EP2018/086394 which is herewith incorporated as a reference in its entirety. In short, the bioreactor is a fixed bed bioreactor comprising a fixed bed. In some embodiments, the fixed bed is a structured fixed bed (which means that it is formed of an easily replicated, generally homogeneous, substantially fixed structure, and thus is not randomly oriented or unstructured, and, as can be appreciated, could take a variety of sizes or shapes while meeting this qualification). In some embodiments, the structured fixed bed described herein can provide for a large cell growth surface within a small volume while still allowing circulation of medium and cells. In some embodiments, the fixed bed is made of structural elements from a material compatible with cell adherence and growth. In some embodiments, the structured fixed bed described herein can comprise a tortuous path for cells and cell culture media. In some embodiments, a spacer layer facilitates the tortuous path. In some embodiments, the structured fixed bed can comprise one or more cell immobilization layers having a surface which allows cells to adhere and grow upon and forming a cell immobilization section. In some embodiments, adjacent to the cell immobilization layers are one or more spacer layers. In some embodiments, the spacer layer can include a structure which forms a spacer section. In some embodiments, the spacer section allows passage of cells and medium through an open but tortuous path. In some embodiments, the structure or nature of the spacer layers can be chosen such that the spacer layers create a tortuous, open path for cells and culture media to travel in parallel to the surface of said spacer and cell immobilization layers. In some embodiments, the tortuous path or channel formed by the spacer section creates turbulence which facilitates cell and cell medium incursion into the immobilization layers.

In some embodiments, the spacer layer can be a mesh or comprises a mesh structure. In some embodiments, mesh structure or mesh can be a structure comprising a network or web-like pattern of filament, wire or thread. In some embodiments, the network can define pores, openings or perforations formed of a three-dimensional weave. In some embodiments, the spacer layers and/or the cell immobilization layers of a spacer section and a immobilization section can be made of a biocompatible polymer, for example polyester, polyethylene, polypropylene, polyamide, plasma treated polyethylene, plasma treated polyester, plasma treated polypropylene or plasma treated polyamide. In some embodiments, the spacer layer or the cell immobilization layer can comprise silica, polystyrene, agarose, styrene divinylbenzene, polyacrylonitrile or latex. In some embodiments, the layers can be hydrophilic or hydrophobic. In some embodiments, the cell immobilization layer can be hydrophilic. In some embodiments, a cell immobilization layer can be woven or nonwoven. In some embodiments, a cell immobilization section and a spacer section can be alternately positioned. In some embodiment, alternately positioned sections can alternate in a vertical position or in a horizontal position. In some embodiments, one or more layers of cell immobilization layers can be superimposed on one or more spacer layers (or vice versa). In some embodiments, a structured bed disclosed herein can be tightly or loosely rolled to a structure such as a spiral structure or varying shape. Further embodiments of the bioreactor will be described in the figures.

In an embodiment, the bioreactor is a modular bioreactor including a fixed bed for culturing cells. Said modular bioreactor comprises:
 a base portion having a first chamber;
 an intermediate portion forming at least part of a second, outer chamber for receiving the fixed bed and at least part of a third inner chamber for returning fluid flow from the second outer chamber to the first chamber; and
 a cover portion for positioning over the intermediate portion.

In an embodiment, the fixed bed comprises a structured fixed bed.

In an embodiment, the intermediate portion comprises a tubular part, the structured fixed bed extending spirally around the tubular part. In an embodiment, the intermediate portion comprises a tubular part formed by an inner wall of the fixed bed. In an embodiment, the intermediate portion comprises a plurality of intermediate parts, each associated with a structured fixed bed.

In an embodiment, at least one of the plurality of intermediate parts is perforated for allowing fluid to flow from a first structured fixed bed below the at least one intermediate part to a second structured fixed bed above the at least one intermediate part.

In an embodiment, each of the plurality of intermediate parts is tubular, and each structured fixed bed comprises a spiral bed wound around the tubular intermediate part.

In an embodiment the system further including a perforated support for the structured fixed bed. In an embodiment, the intermediate portion further includes a tubular casing for forming a periphery of the modular bioreactor, the tubular casing forming a space for heating, cooling, or insulating the bioreactor. In an embodiment, the intermediate portion comprises a plurality of intermediate parts, each adapted for connecting with each other. In an embodiment the intermediate portion includes a tube for engaging at least one intermediate part and forming an inner wall of the outer second chamber for receiving the fixed bed. In an embodiment, the tube engages a first intermediate part below the tube and a second intermediate part above the tube.

In an embodiment, the second intermediate part includes openings for creating a fluid film along the third inner chamber. In an embodiment the system further including supports for supporting the second intermediate part from the first intermediate part. In an embodiment the supports comprise vertical rods.

In an embodiment the cover portion comprises a removable cap including a plurality of ports. In an embodiment the removable cap has an outer diameter that is less than an outer diameter of the intermediate portion. In an embodiment at least one of the ports includes a threaded metal insert. In an embodiment the cover portion has an outer diameter that is equal to or greater than an outer diameter of the intermediate portion.

In an embodiment, the intermediate portion comprises an intermediate part adapted for positioning at least partially within the base portion, the intermediate part further including a flow disruptor for disrupting fluid flow.

In an embodiment, the base portion includes a further chamber radially outward of the first chamber in fluid communication with the second outer chamber including the fixed bed, which is formed by an upstanding wall having a plurality of openings for transmitting fluid from the first chamber to the further chamber.

In an embodiment, the bioreactor further includes an agitator associated with the base portion. In an embodiment, the intermediate portion is adapted for suspending the agitator in the first chamber in a manner that allows side-to-side movement for alignment with an external drive.

In an embodiment the bioreactor further includes a container for containing the agitator, the container including a central inlet and a plurality of radially oriented outlets. In an embodiment the agitator comprises a plurality of curved blades.

In an embodiment, a flow divider is associated with the central inlet. In an embodiment the bioreactor further includes a plurality of flow disruptors for dividing the fluid flow entering the third inner chamber into a plurality of streams. In an embodiment, the plurality of flow disruptors are associated with a ring.

In an embodiment, the bioreactor further includes one or more conduits for permitting gas to enter into a space behind one of the streams. In an embodiment one or more conduits are connected to a structure including the plurality of flow disruptors. In an embodiment, a first conduit is connected to the structure. In an embodiment, the first and second conduits are connected to the structure.

In an embodiment the first and second conduits are not connected to the structure.

In an embodiment, the modular bioreactor comprises a base portion connected to both a central column and an outer casing, the outer casing and central column together forming a compartment for culturing cells. In an embodiment the compartment includes at least one structured fixed bed. In an embodiment the compartment includes a plurality of structured fixed beds, arranged in a stacked configuration.

In an embodiment, the bioreactor further includes an intermediate part between at least two of the plurality of structured fixed beds. In an embodiment the at least one structured fixed bed comprises a spiral bed. In an embodiment, each of the plurality of stacked, structured fixed beds is wrapped around the central column.

In an embodiment, the central column comprises first and second interconnected tubes, a first structured fixed bed of the plurality of structured fixed beds being wrapped around the first tube and a second structured fixed bed of the plurality of structured fixed beds being wrapped around the second tube. In an embodiment the central column comprises first and second tubes for engaging a perforated support extending between at least two of the plurality of structured fixed beds.

In an embodiment the fixed bed comprises a cartridge adapted for being inserted into and removed from the second, outer chamber or compartment.

In an embodiment the base portion is removably connected to the central column. In an embodiment the base portion is removably connected to the outer casing.

In an embodiment, the system comprises a bioreactor for culturing cells, comprising:
a base part having a first chamber including an agitator for agitating a fluid; and
a first central column removably attached to the base part, the first central column forming at least part of a second, outer chamber for culturing cells and a third inner chamber for returning fluid flow from the second outer chamber to the first chamber.

In an embodiment the second, outer chamber includes a first structured fixed bed. In an embodiment the first structured fixed bed comprises a spiral bed.

In an embodiment, the first structured fixed bed is wound around the first central column.

In an embodiment, the bioreactor further includes a second central column forming at least part of the second outer chamber, and further including a second structured fixed bed spaced vertically from the first structured fixed bed.

In an embodiment the bioreactor further includes a perforated support between the first structured fixed bed and the second structured fixed bed.

In an embodiment the second, outer chamber includes an unstructured bed.

In an embodiment, the system comprises a bioreactor for culturing cells in connection with a fluid, comprising:
a first chamber including an agitator for agitating the fluid;
a second, outer chamber including a plurality of stacked beds for culturing cells; and
a third, inner chamber for returning fluid from the second outer chamber to the first chamber.

In an embodiment, said bioreactor has a base portion having the first chamber;
an intermediate portion forming at least part of the second, outer chamber and at least part of the third inner chamber; and
a cover portion for positioning over the intermediate portion.

In an embodiment the intermediate portion comprises a first support for supporting a first bed of the plurality of stacked beds. In an embodiment the intermediate portion comprises a second support for supporting a second bed of the plurality of stacked beds. In an embodiment, the intermediate portion is adapted for removably connecting with the base portion and the cover portion.

In an embodiment the second, outer chamber is bounded by an outer wall, and further including an outer casing forming a space with the outer wall, the space being for insulating, heating, or cooling the second, outer chamber.

In an embodiment, the system of the current disclosure comprises a bioreactor for culturing cells in connection with a fluid, comprising:
a first chamber including an agitator for agitating the fluid;
a second, outer chamber including at least one bed for culturing cells; and
a third, inner chamber for returning fluid from the second outer chamber to the first chamber,
wherein the second, outer chamber is bounded by an outer wall, and further including an outer casing forming a space with the outer wall, the space being for insulating, heating, or cooling the second, outer chamber.

In an embodiment the at least one bed comprises a structured fixed bed. In an embodiment the structured fixed bed comprises a spiral bed. In an embodiment the inner chamber is formed by at least one tube.

In an embodiment the at least one tube is connected to first and second supports bounding the at least one bed. In an embodiment the first and second supports are connected to the outer wall. In an embodiment the first and second supports are at least partially perforated.

In an embodiment, the system according to the current disclosure comprises an apparatus for culturing cells, comprising:
a bioreactor including an agitator, the bioreactor adapted for maintaining the agitator in a suspended condition that allows side-to-side movement for alignment with an external drive.

In an embodiment, the bioreactor includes a base portion for receiving the agitator, and an intermediate portion for supporting a carrier for carrying the agitator in the suspended condition. In an embodiment the carrier comprises a clip for engaging the intermediate portion.

In an embodiment, the system according to the current disclosure comprises a bioreactor including an agitator having a plurality of curved blades.

In an embodiment the agitator includes a central open region radially inward of the plurality of curved blades. In an embodiment the agitator includes one or more magnets. In an embodiment the blades are curved in a radial direction.

In an embodiment, the system according to the current disclosure comprises a bioreactor comprising first and second stacked, structured beds. In an embodiment, said bioreactor further includes a screen engaging both the first and second stacked, structured beds. In an embodiment the first and second stacked, structured beds comprise spiral beds.

Access to a bioreactor described herein can be via a lid, or door. In some embodiments, an access mechanism for the bioreactor can comprise for example, a lock and key mechanism, a pass code punch pad, card swipe, transponder reader, finger print scanner, retina scanner, sensors, automatic identification and data capture methods such as radio-frequency identification (RFID), biometrics (like iris or facial recognition system), magnetic stripes, Optical character recognition (OCR), smart cards, voice recognition, or any other access mechanism.

In some embodiments, the bioreactor lid is designed such that it allows access to the fixed bed for fixed-bed sampling for in-process control and for end of process analysis. In some embodiments, the lid comprises ports that are adapted for aseptic sampling for cells and metabolites. In some embodiments, samples comprise the fixed bed or a portion similar to but separate from the fixed bed.

In some embodiments, the bioreactor disclosed herein can comprise and or contain sensors for monitoring different parameters. In some embodiments, a sensor disclosed herein can be located in any compartment of a bioreactor disclosed herein. In some embodiment, sensors described herein can be a gas sensor (e.g. oxygen, nitrogen, or carbon dioxide), pH sensor, temperature sensor, cell density sensor, or dissolved oxygen sensor. In some embodiments, the sensors disclosed herein can measure amongst other things, biomass or cell density, the dissolved oxygen partial pressure, oxygen content, the $\rho T1$ value, the temperature, certain concentrations of nutriments, such as lactate, ammonium, carbonates, glucose or any metabolic product or product to be metabolized which could for example reflect the cell density. In some embodiment, cell density (biomass density) can be determined by electrical impedance analysis or electrical impedance spectroscopy using an arrangement of measuring electrode. In some embodiments, a bioreactor according to the disclosure can comprise sensors for measuring culture parameters. In some embodiments, a sensor disclosed herein can be in contact with culture medium in the bioreactor. In some embodiments, culture parameters can comprise amongst other things, the dissolved oxygen partial pressure, the pH, the temperature, the optical density, certain concentrations of nutriments, such as lactate, ammonium, carbonates, glucose or any metabolic product or product to be metabolized which could for example reflect the cell density. In some embodiment, a bioreactor disclosed herein can use regulation loops according to the disclosed parameters. In some embodiments, a regulation loop can for example, modulate the quantity of oxygen to be injected according to the value of the dissolved oxygen partial pressure present or the quantity of dissolved oxygen consumed by the cells; speed of circulation of the culture medium; inject CO2 according to the pH value obtained by the sensors or any other type of regulation generally used in this type of culture. In some embodiments, cells can be exposed to dissolved oxygen concentrations of 300 µM or less (160 mmHg partial pressure), less than 200 µM, or between 20 and 150 µM. In some embodiments, cells can be exposed to about 0%, 1%, 5%, 10%, 20%, 30%, 40%, 50%, 60%, 70%, 78%, 80%, 90%, or 100% nitrogen and/or about 0%, 1%, 5%, 10%, 21%, 30%, 40%, 50%, 60%, 70%, 80%, 90% or 100% oxygen. In some embodiments, cells can be exposed to pure oxygen or an oxygen enriched atmosphere.

In some embodiments, a bioreactor disclosed herein may comprise heating and/or cooling devices, designed to heat and/or cool culture medium. In some embodiments, the heating device can be an electrical element, an electrical coil or any other heating means generally used in the field of cell culture, such as for example a thermostatically controlled double jacket. In some embodiments, cooling device may be any suitable cooling devices such as a Peltier element.

In some embodiments, culture medium can be circulated via an agitator. In some embodiments, and agitator can be a rotatable, (non-contact) magnetic impeller, a blade or screw agitation system, or an external circulation system. In some embodiments, the agitator can comprise a disk blade turbine, a curved blade turbine, an open lade fluid foil axial impeller, a turbine impeller with pitched blades, or a three-blade propeller. In some embodiments, the agitator can have a flow rate of less than about 0.01 l/min, 0.05 l/min, 0.1 l/min, 0.5 l/min, 1 l/min, 2 l/min, 5 l/min, 10 l/min, 15 l/min, 20 l/min, 50 l/min, 100 l/min, or 150 l/min to more than about 160 l/min, 180 l/min, 200 l/min, or 250 l/min. In some embodiments, the impeller is designed for single-use only.

The bioreactor of the current system will be provided with at least one inlet for allowing entrance and exit of gasses and liquid. In some embodiments, said bioreactor will comprise at least one inlet for the introduction of gas and/or culture medium and at least one outlet for the collection of the culture medium contained in the bioreactor. In some embodiments, mix of gas or gaseous mixture and culture medium can be supplied to through the same supply line. In an embodiment, the bioreactor will be provided with pre-fitted tubing manifolds allowing a liquid inlet and a liquid outlet as well as base addition and gas vents. In an embodiment, the bioreactor assembly consisting of the bioreactor vessel itself and each tubing manifold is a closed system ensuring sterility post autoclave treatment. The connection of each tubing manifold to external containers (e.g. culture medium, base bottle, inoculum) prior to the start of the cell culture is made possible by non-aseptic male-female fluid connectors/disconnectors. In an embodiment, syringes or equivalent assemblies can be fitted on the bioreactor outlet line in order to allow sampling of the liquid media.

In an embodiment a bioreactor kit is provided, wherein the kit comprises a bioreactor as described herein and one or more tubing manifolds pre-fitted to the bioreactor, thereby forming a closed system ensuring sterility post autoclave treatment In an embodiment, the docking station is provided with locations suitable for achieving bottles such as base bottles, harvest bottles, alkali bottles, etc. In an embodiment, a set of caps pre-fitted with the required tubings, connectors and fitters will be provided which can be fitted onto these bottles and further be connected to the bioreactor or other parts of the system.

In an embodiment, the system is provided with a retention tray for catching potential liquid overflows.

In a further embodiment, the currently disclosed system comprises a concentrator fitted in the docking station. The concentrator allows to increase the amount of target biomolecule present in the liquid by enabling the reduction of the total liquid volume in the system without reducing the amount of target molecule in the liquid. Accordingly, implementation of a concentrator in the system of the disclosure further reduces the amount of space occupied by the system as it allows to reduce the volume of the liquid. In some embodiments, the concentrator comprises a tangential flow filter or a dead-end filter. In some embodiment, the concentrator is based on filtration and/or size exclusion chromatograph. In some embodiments, the concentrator can be a filtration device, a micro-filtration device, or an ultra-filtration device or a combination of both micro- and ultra-filtration device. Preferably, the concentrator comprises a filtration device or a size exclusion chromatography device.

In the current system, the concentrator is equipped with a retentate conduit suitable for collecting the retentate comprising the largest fraction of target biomolecules, and which allows re-circulation of that retentate to an input of the bioreactor or to an input of an intermediate vessel positioned between the concentrator and the bioreactor. The current system thus allows re-circulating of the concentrated retentate for further concentration of the biomolecule by allowing re-circulation of the retentate through the same concentrator. In an embodiment, the liquid is re-circulated through the concentrator at least 5 times, preferably at least 10 times, more preferably at least 15 times, most preferably until the desired reduction in cell culture harvest is reached. This set up allows the system to reduce the amount of downstream processes needed as a highly concentrated biomolecule product is obtained due to re-circulation of the retentate. In an embodiment, the conduits of the system comprise pumps, valves and flow meters or sensors to control and monitor the flow of liquid from, for example, the concentrator to the bioreactor and/or intermediate vessel. In an embodiment, the system's conduits, such as the retentate conduit, comprise detectors (e.g., optical detectors). In an embodiment, the detectors can monitor the amount of cells, target biomolecules, and/or contaminants that are transported in the conduits.

In an embodiment, the docking station will be provided with an intermediate vessel, positioned between the bioreactor and concentrator, and fluidly connected to both bioreactor and concentrator. The volume of the intermediate vessel is preferably adapted to the volume of the bioreactor. The retentate comprising the concentrated target biomolecule is eventually harvested in the intermediate vessel. When, for example, the system is equipped with a bioreactor with a capacity of around 10 L that uses 300 L of culture medium in perfusion mode, that system will preferably be equipped with an intermediate vessel with a volume of around 10 L.

In an embodiment, the bioreactor and the concentrator are connected by a conduit facilitating liquid transport from said bioreactor to said concentrator. Alternatively, when an intermediate vessel is included in the system, the bioreactor and the intermediate vessel are connected by a conduit, facilitating liquid transport from the bioreactor to said intermediate vessel. In addition, the intermediate vessel and the concentrator are also connected by a conduit which allows liquid transport from the intermediate vessel to the concentrator. Finally, a conduit facilitating liquid transport from the concentrator to the bioreactor can also be provided. In an embodiment the intermediate vessel may be single-use, disposable and/or autoclavable.

The system's concentrator can be a chosen from a number of devices known to the skilled person which are suited for reducing the volume of the liquid in which the target biomolecule resides. In some embodiments, the concentrator comprises one type of concentration device (e.g., tangential flow filter). In some embodiments, the concentrator comprises more than one type of concentration device (e.g., tangential flow filter and dead-end filter). Most of these devices are based on filtration and/or size exclusion chromatography. In one embodiment the concentrator is a filtration device, more preferably a micro-filtration device, or an ultra-filtration device or a combination of both micro- and ultra-filtration device. When the system is provided with an ultra-filtration device for reducing the volume of the liquid in which the target biomolecule resides, the membrane of the device is adapted as to allow flow through of water and low molecular weight solutes, which are in general referred to as the permeate, while macromolecules such as biomolecules are retained on the membrane in the retentate. In a further embodiment, the system is provided of a tangential flow filtration device (TFF). In an embodiment, said TFF is equipped with at least one hollow fiber having pores with a porosity sufficient to retain practically all of the target biomolecules, while permitting smaller contaminants such as growth medium and solutes to pass through the pores of the membrane. In contrast to dead-end filtration, in which the liquid is passed through a membrane or bed, and where the solids are trapped on the filter, tangential flow across the surface of the filter is allowed in the TFF device, rather than directly through the filter. Accordingly, formation of a filter cake in the TFF is avoided. In another embodiment, said TFF may be equipped with a cassette/cartridge allowing tangential flow filtration. In yet another embodiment, said TFF is a single pass tangential flow filtration (SP-TFF). This device is especially advantageous when purifying proteins such as antibodies. In some embodiments, the TFF comprises a membrane with an area of between about 1000 $cm^2$ and 2000 $cm^2$, preferably about 1500 $cm^2$. The TFF may be reused, for one time use and/or disposable. In some embodiments, the TFF is plug and play.

In a further embodiment, a kit is provided, wherein the kit comprises a TFF cartridge and one or more pre-assembled manifolds. Preferably the one or more manifolds comprise tubing, sterile connectors and optionally one or more pressure sensors. In one embodiment, the one or more pressure sensors are disposable.

As mentioned above, the system is provided with a retentate conduit mediating re-circulating of the retentate to an input of the bioreactor or an input of an intermediate vessel. An additional advantage of implementing a TFF device as a concentrator in the system is that the TFF device is suited to be operated in a continuous perfusion process. This allows significant concentration of the culture volume. For example, when starting from a fixed bed perfusion bioreactor with a 30 $m^2$ internal growth area (referring to the surface area accessible for cell growth), the system allows concentrating the culture volume to a final volume of 50 L. This is the equivalent of 360 roller bottles based culture or 12 large cell factories and thus a significant improvement over the prior art, not in the least as it allows reduction of the footprint of the system. The size reduction of the system allows for production of biomolecules to be performed in a highly contained and sterile environment, assuring the sterility of operations.

In an embodiment the conduits of the system are fitted with one or more pumps to provide directional liquid flow and to allow control or induce differential pressure between different parts of the system. In a further embodiment, the pumps can operate both forward and backwards. In a still further embodiment, the conduits of the system are preferably fitted with one or more pumps to provide cross-flow of the liquid through the concentrator.

The conduits of the system here disclosed, may be provided with sensors for measuring parameters important for cell growth and for the purification process including but not limited to liquid flow rate, temperature, pH, oxygen saturation and pressure. In addition conduits of the system may be provided with valves to control flow distribution. The valves further allow engaging or disengaging a specific system segment or conduit. In some embodiments, the valves are metered valves or discrete valves (e.g., on or off valves). In an example, the valves are discrete valves. In some embodiments the valves allow sampling of the liquid from the respective conduit, for example for quality control.

In an embodiment, the intermediate vessel will be provided with liquid level sensors, for controlling the volume in the vessel during perfusion with the concentrator. In an embodiment, a low level and high level sensor will be provided. When the perfusion with concentrator sequence such as a TFF is started, a constant concentration of $CO_2$/Air gas is added to the intermediate vessel in order to have a constant pH in the intermediate vessel. When the volume reaches the low level in the vessel, a concentrator pump starts at low speed setpoint of the pump, and the concentrator valve stays open at 100%. When the high level is reached, the filtration of the concentrator will increase to decrease the level in the concentration bottle. To achieve this, the concentrator pump will increase its throughput to a selected speed setpoint and the transmembrane pressure of the concentrator may be selected by varying the opening the concentrator valve. When the volume in the intermediate vessel is back to a low level, the concentrator pump will be set again at a low speed setpoint and the concentrator valve will be opened again 100%.

In an embodiment, the system is provided with a pre-filter which is positioned between the bioreactor and the concentrator. In some embodiments, the pre-filters may have the same porosity or the pre-filters may have different porosities. In an example, the system has at least 2 pre-filters of differing porosity. The pre-filter prevents clogging of the concentrator. The pre-filter thereto preferably has a pore size of at least 50 µm, at least 75 µm, at least 100 µm, at least 125 µm and at most 250 µm, at most 200 µm, at most 175 µm, at most 150 µm. In a preferred embodiment the filter has a pore size of 125 µm. A pore size which is smaller than 50 µm will not permit sufficient liquid flow rate whereas a pore size which is above 250 µm would risk the flow through of liquid containing particles which might clog the system. In an embodiment, the pore size of the pre-filters is significantly larger than the biomolecule and is sized to retain cells debris and aggregates. In an embodiment, said pre-filter may be a TFF, wherein the particles larger than said biomolecule of interest are retained, whereas smaller particles, including the biomolecule, will pass through said TFF. In another embodiment, said pre-filter may be an adsorption system, for example an adsorption system based on chromatography.

When an intermediate vessel is included in the system, the pre-filter described above is preferably positioned between the bioreactor and the intermediate vessel. Accordingly, the system allows that the conduits between the intermediate vessel and the concentrator remain free of particles which due to their size could potentially clog the concentrator.

Undesired material that is produced in the system or by-products of the process can be temporarily stored in a decontamination vessel. The system may comprise one or more decontamination vessels and may be adapted with suitable conduits such as an output conduit line from the concentrator to the decontamination vessel(s) in order to discard the permeate. Another example is an output conduit line from the bioreactor to the decontamination vessel to directly discard liquids before the production of the biomolecule has started (e.g. before viral infection of the cells). In an embodiment, the decontamination vessel(s) is/are inside the docking station. In another embodiment, said decontamination vessel(s) is/are located outside the docking station.

In addition to the production and purification of biomolecules (e.g. upstream production processes), the system can be adapted to be combined with devices suitable for performing downstream production processes. In an embodiment, these additional devices will be located outside the docking station and will be connectable to the docking station or units within the docking stations via tubings and manifolds.

The system of the disclosure can be connected to any unit suitable for downstream processing such as a clarification unit, chromatography unit, polishing unit or (viral) inactivation unit, depending on the downstream requirements of the product that is produced. Conduits facilitating liquid transport from the docking station or units therein to the downstream units can be provided.

The system as described is designed to be used for the growth of adherent and non-adherent cells. Adherent cells grown in the system may be used to produce viral vaccines (both human and veterinary) and viral vectors, whereas non-adherent cells allow the production of other proteins and biological materials.

In an embodiment the process flow is controlled by a process controller or process control device present in the docking station. Integration of the controller in a docking station allows to maintain the compactness of the system when it is included in the system. In an embodiment, the housing of the controller is thus designed to allow being used as docking station of the system as described.

The controller controls and operates bioreactor parameters as well as process flow parameters and monitors and records data from one or more sensors described above (pH, temperature and/or DO). In an embodiment, the controller is able to control the pH in the bioreactor and system in a range of between 4 to 9. In an embodiment, the controller is able to control the dissolved oxygen (DO) concentration from 0 to 100%, preferably by using a resolution of +−5%. In an embodiment, the controller is able to control the temperature from 23 to 40% using a resolution of +−0.1° C.

Said controller furthermore controls the functioning of the concentrator and the recirculation of retentate from concentrator to intermediate vessel and back. To that purpose, said controller is provided with software allowing monitoring, controlling and recording the process flow and parameters of the system. The controller is able to manage liquid flow through the subsequent parts of the system thereby controlling the production and purification of the target biomolecule. Preferably, liquid flow is managed by the controller in the system by controlling the functioning of the pumps and or valves present therein. In an embodiment the process control device provides automated control of the system's process flow. In an embodiment, the controller can record and report data obtained from the sensors.

Access to the controller can be provided to the user via a computer which can be connected to the controller. The controller allows export of data through one or more data transfer devices which can be wireless such as a Wifi or Bluetooth connection or wired such us a USB connection present on said controller. Data connections on the controller can in another or further embodiment allow access to an IT network. In an embodiment, a user interface in the form of a screen is connected to the controller which allows the system's user or operator to follow the process flow and measured parameters as well as to manually operate the system, e.g. by starting or stopping certain sub-processes. In an embodiment, the screen is located onto the docking station. Said screen may be a touch screen.

In some embodiments, the controller comprises a power, data and gas (PDG) management box. Preferably the PDG is adapted to provide filtered air, $CO_2$, $O_2$ and/or other gases.

Due to the optimization of each unit in the system of the present disclosure, the compact structure of each compartment allows all compartments belonging to the system to be incorporated in a single cabinet, flow, isolator or containment enclosure. This not only contributes to reduction of space required but also to the enhanced safety when using this system. In addition, the connections between the compartments allow the production and purification steps to be performed without exiting the containment enclosure thus ensuring minimal safety risks.

The compact structure of the system further allows, in another or further embodiment, to provide the system as a portable system for biomolecule production and purification system e.g. in a container or trailer. Therefore, the current system can be a mobile system. In another or further embodiment, the compartments of the platform can also be mobilized, for example, by placing each compartment or isolator on a mobile skid. In yet another embodiment, the system can be assembled in a modular fashion.

In a second aspect the disclosure provides a method for producing biomolecules, wherein said system comprises a bioreactor comprising a liquid comprising cells, said method comprises a concentration step, wherein output from said bioreactor is concentrated in a concentrator and wherein output from said concentrator is recirculated to said bioreactor or to an intermediate vessel positioned between said concentrator and said bioreactor. It will be apparent to a skilled person that the system as described in one of its embodiments is suited for executing said method.

In an embodiment, the method for producing biomolecules according to the present disclosure makes use of pumps and valves, which are fitted on the conduits of the system, to induce directional flow of the liquid through the system and to allow reversible engaging and disengaging of different segments of the system. In some embodiments, the disclosed method makes use of an ultrafiltration device in the concentrator. To avoid clogging of the ultrafiltration device present in the concentrator, the liquid may in an embodiment first passed through a pre-filter which removes large solid particles from the liquid but is permeable to the biomolecule of interest. In some embodiments, the pre-filter has a pore size of approximately 125 µm and a cutoff of approximately 100 kDa. Preferably, the recirculated retentate is harvested in an embodiment of the method by collecting it in the intermediate vessel, thereby obtaining a concentrated cell culture harvest. In an embodiment, parts of the system such as the bioreactor and the intermediate vessel may be provided with one or more sensors for measuring for instance but not limiting to the pH, temperature and the dissolved oxygen. Accordingly, the bioreactor and intermediate vessel may allow control of pH, and temperature of the concentrated cell culture harvest.

Optionally, the pH of the concentrated cell culture harvest is adjusted to the desired value for downstream processes. In addition an optional endonuclease treatment can be performed on the concentrated cell culture harvest to degrade DNA and RNA present in the concentrated cell culture harvest while leaving proteins intact. An endonuclease treatment step can contribute to the prevention of aggregation in the concentrated cell culture harvest, thus providing optimal conditions for further downstream processing.

In an embodiment, said method further comprises downstream processing steps which can include clarification of the concentrated cell culture harvest thereby obtaining a clarified cell culture harvest and/or subsequent purification of the desired biomolecule by performing a chromatography step on the clarified cell culture harvest.

As mentioned above, the currently disclosed method can be performed in a restricted amount of space due to the compactness of the required equipment, and thus can be performed within isolators such as a laminar flow. Therefore, the method of the present disclosure is especially well suited to purify biomolecules, such as cells, proteins (antibodies) and viruses. In that last case, the method further includes a virus inactivation step performed on the purified viral product, preferably consisting of treatment of the virus with an inactivation composition. The inactivation compositions are selected from the group comprising formaldehyde, at least one detergent, at least one acid or any combination thereof. Other inactivation compositions may comprise a potassium persulfate solution (commercially known as Virkon®), sodium hydroxide or bleach. Preferably, formaldehyde or formalin is used for viral inactivation.

Accordingly, in an embodiment of the disclosed method, the purified biomolecule is a purified inactivated virus, used for the formulation of a vaccine, such as for example an inactivated polio virus vaccine. The method of the disclosure is especially well suited for the production and purification of biomolecules wherein the biomolecules are viruses or inactivated viral particles.

It is supposed that the present invention is not restricted to any form of design described previously and that some modifications can be added to the presented examples without reappraisal of the appended claims. For example, the present invention has been described referring to Polio vaccine, but it is clear that the invention can be applied to Rotavirus vaccine, for instance or to Rabies vaccine.

DETAILED FIGURE DESCRIPTION

FIG. 1 shows a schematic overview of a system for producing biomolecules according to an embodiment of the disclosure.

The schematic overview is shown of a system for producing biomolecules comprising a bioreactor (1) comprising a cell culture; a concentrator (2), wherein said concentrator is equipped with a retentate line output (300) which collects the concentrator output and which allows re-circulating of the output to an input of said bioreactor (1). The bioreactor (1) and the concentrator (2) are connected by a conduit (301) facilitating liquid transport from said bioreactor (1) to said concentrator (2). To avoid clogging of the concentrator (2), the liquid is first passed through a pre-filter (7) which removes large solid particles from the liquid but is permeable to the biomolecule of interest. The conduits of the system are fitted with pumps (5) to provide directional liquid flow, for controlling or inducing differential pressure between different parts of the system and to provide crossflow of the liquid through the concentrator (2). In addition, the conduits of the system are provided with valves (6) to control flow distribution. The valves further allow to engage or disengage a specific system segment or conduit. Finally, an output conduit (302) line from the concentrator (2) to a decontamination vessel (8) is provided to discard the permeate. The decontamination vessel (8) comprises at least one waste container (such as a tank) where undesired material that is produced in the system or by-products of the process can be temporarily stored.

The concentrator provides for an increase of the amount of target biomolecule present in the liquid by enabling the reduction of the total liquid volume without reducing the amount of target molecule in the liquid. The current embodiment of the disclosed system thus provides for re-circulating of the concentrated liquid retentate comprising the target biomolecule, for further concentration of the biomolecule by allowing re-circulation of the liquid through the same concentrator (2). This set-up allows for the design of the overall system to fewer numbers of downstream processes needed as a highly concentrated biomolecule product is obtained due to re-circulation of the liquid.

Figure 2A:
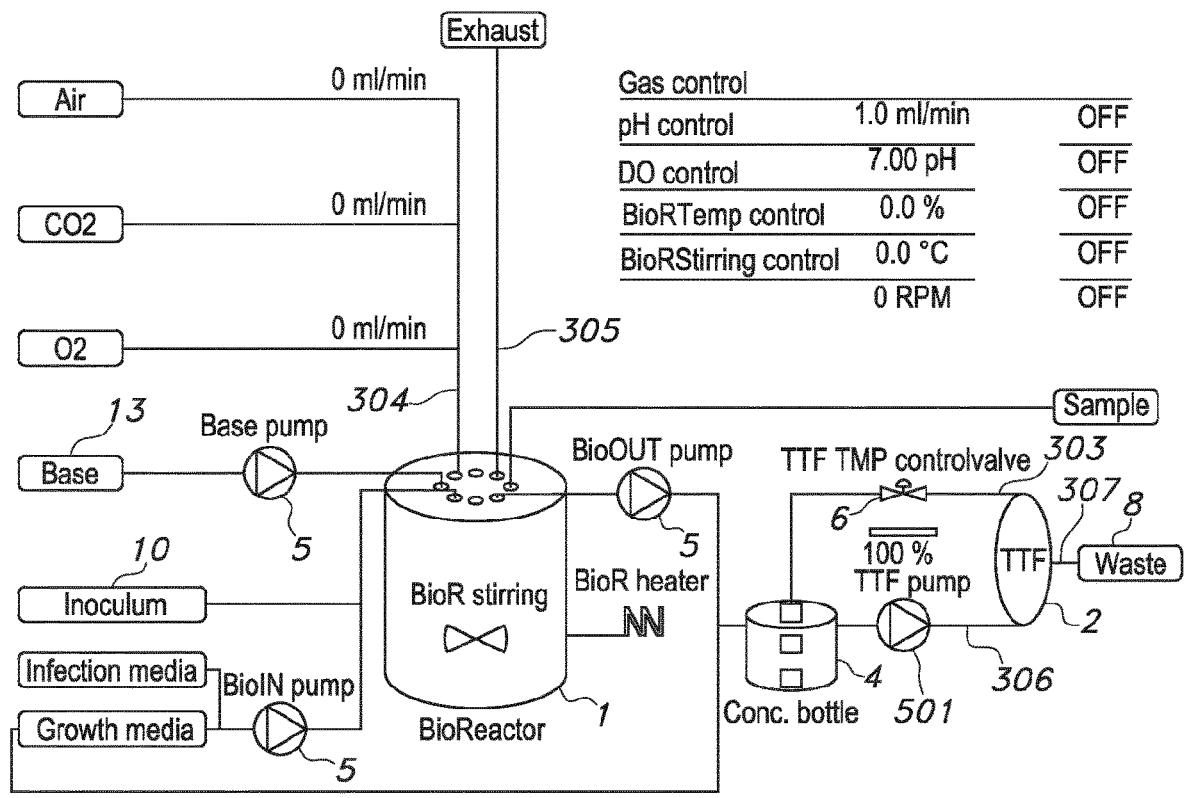
FIG. 2A shows a schematic overview of a system for producing biomolecules according to another embodiment of the disclosure.

FIG. 2A shows a schematic overview of a system for producing biomolecules according to another embodiment of the disclosure.

The schematic overview is shown of a system for producing biomolecules comprising a bioreactor (1) including a chamber suitable for receiving a liquid comprising cells, and a concentrator (2), wherein said concentrator is equipped with a retentate line output (303) which collects the concentrator output and which allows re-circulating of the retentate output to an input of an intermediate vessel (4) or concentrator bottle positioned between said concentrator (2) and said bioreactor (1). The bioreactor (1) and the intermediate vessel (4) are connected by a conduit, facilitating liquid transport from the bioreactor (1) to said intermediate vessel (4). Alternatively, an additional conduit connected directly from the bioreactor (1) to the concentrator (2) could be present (not shown on figures) for transporting liquid from the bioreactor (1) to the concentrator (2). In addition, the intermediate vessel (4) and the concentrator (2) are also connected by a conduit (306) having pump (5) which facilitates liquid transport from the intermediate vessel (4) to the concentrator (2). The concentrator enhances the amount of target biomolecule present in the liquid by enabling the reduction of the total liquid volume without reducing the amount of target molecule in the liquid.

In an embodiment two gas connections are present, one connection (304) entering the bioreactor (1) and one connection (305) exiting said bioreactor (1). The bioreactor (1) is further connected with the inoculum vessel (10) comprising the rinsed, detached and neutralized cell preculture in suitable growth medium, and a base (13) inlet for regulation of the pH inside the bioreactor (1).

Multiple types of concentrators are suitable for use in the system, the system according to this embodiment, is provided with a tangential flow filtration device (TFF) acting as the concentrator. The TFF is equipped so that it retains practically all of the target biomolecules, while permitting smaller contaminants such as growth medium and solutes to pass through the pores of the membrane. To that purpose and in a possible embodiment, said TFF may be provided with at least one hollow fiber having pores with a specific porosity, e.g. a porosity sufficient to retain practically all of the target biomolecules in the retentate, while permitting smaller contaminants such as growth medium and solutes to end up in the permeate. The TFF concentrator (2) mediates re-circulating of the retentate comprising the target biomolecule to an input of the intermediate vessel (4). An output conduit (307) line from the TFF concentrator (2) to a decontamination vessel (8) is provided to discard the permeate. The decontamination vessel (8) comprises at least one waste container such as a tank where undesired material that is produced in the system or by-products of the process can be temporarily stored. The system conduits are fitted with pumps (5, 501) and valves (6) to provide directional liquid flow, to control differential pressure between different fragments of the system and to provide cross-flow of the liquid through the TFF concentrator (2).

The concentrator (2) increases the amount of target biomolecule present in the liquid by enabling the reduction of the total liquid volume without reducing the amount of target molecule in the liquid. Reduction of the liquid volume by the system allows down-scaling of the infrastructure required for biomolecule production on an industrial level, thereby also reducing the amount of consumables. In addition, the TFF concentrator (2) of this system is operated autonomously in a continuous perfusion mode. This results in a minimization of human intervention, thereby limiting the safety risks and reducing expenditures.

Figure 2B:
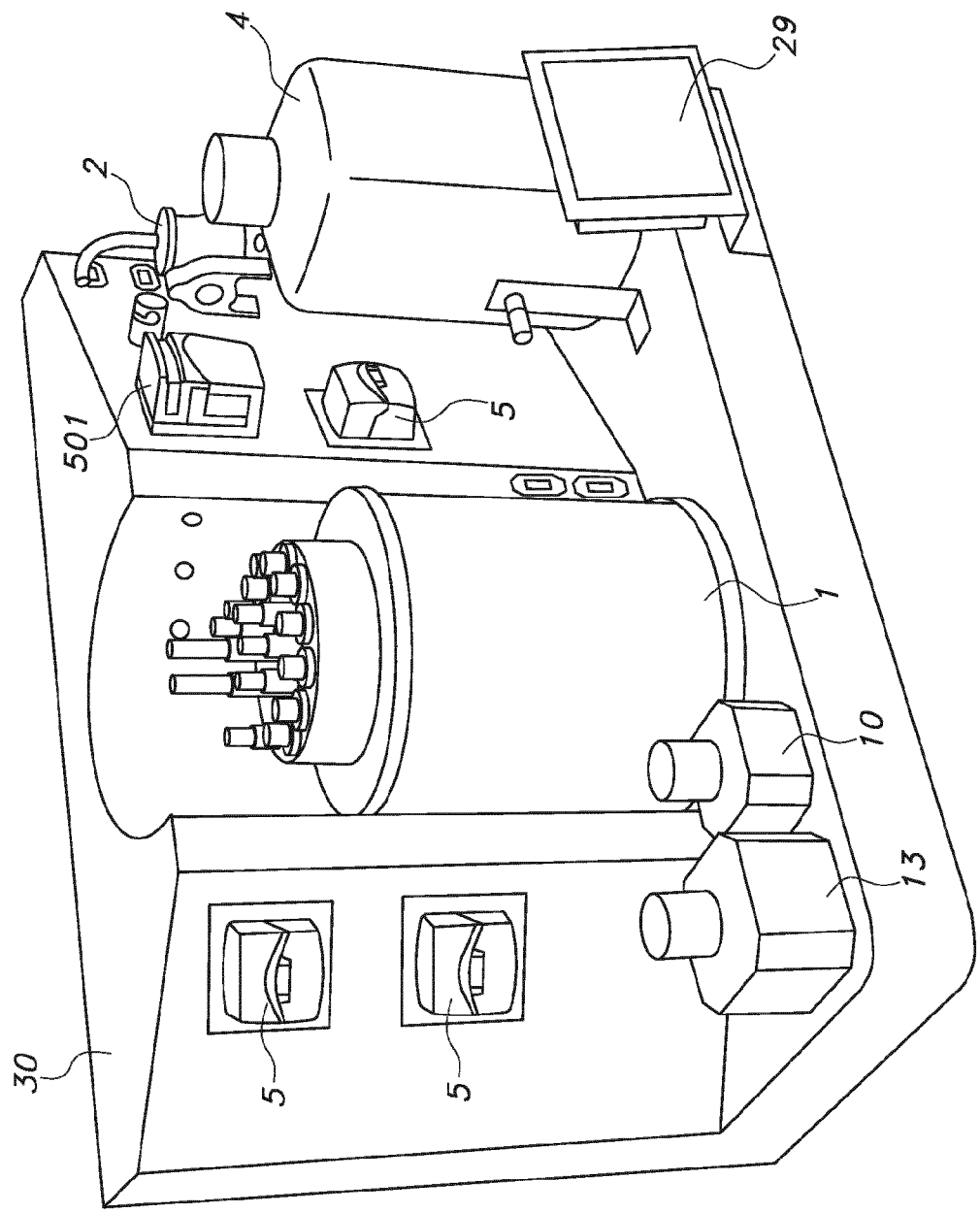
FIG. 2B shows an embodiment of a system able to execute the scheme given in FIG. 2A.

FIG. 2B shows a system able to execute the scheme shown in FIG. 2A.

The system is designed to be used in a biosafety cabinet or isolator and can be used for both process development work and pilot-scale production of biological material, in which case it can be used to produce material for clinical trials as well as low volume commercial production. The system is designed to be used for the growth of adherent cells, as well as non-adherent cells. To that purpose, the system comprises a bioreactor (1), preferably a fixed bed bioreactor. The fixed bed of the bioreactor can be provided with structural elements for allowing growth of the cells on the surface of said elements. An example of such elements is given in PCT/EP2017/078775 which is incorporated herein by reference and which describes a spiral structure for allowing growth of cells and promoting fluid distribution and turbulence. The elements can be made of polyethylene, preferably hydrophilized polyethylene. In an embodiment the bioreactor (1) is for single-use only. Conduits present in the system for liquid or gas transport are not shown in the figure. The bioreactor (1) has at least two fluid connections, wherein one connection allows entrance of fluid into the bioreactor and a second connection allows removal of fluid. This last connection is designed in such way that it minimizes dead space inside the bioreactor (1) once emptied. In a further embodiment, said bioreactor (1) is provided with gas connections, for allowing entrance and/or exit of gas. In a preferred embodiment, three gas connections are present, two connection entering the bioreactor (1) and one connection exiting said bioreactor (1). Advantageously, the bioreactor (1) is furthermore designed to allow sampling for both in-process control and for end of process analysis, preferably from the top of said bioreactor (1). Sampling can occur via syringes or equivalent assemblies.

Circulation in the bioreactor (1) is achieved by use of an impeller, preferably a magnetically driven impeller. A heating element may be present to heat the content of said bioreactor (1), or to heat medium that is brought into said bioreactor (1). The lid of the bioreactor (1) is provided with one or more sensors for measuring temperature, pH and/or dissolved oxygen in said bioreactor (1).

Liquid output from the bioreactor (1) will be transferred by means of a conduit to an intermediate vessel (4) also known as concentrator bottle. Such intermediate vessel (4) may be a PET bottle, and may hold a volume of about 500 mL to 5000 mL. This intermediate vessel (4) is connected to a concentrator (2) which may be a TFF. Liquid from the intermediate vessel (4) comprising the target biomolecule will be transported to the concentrator (2) by means of a pump (501). Said pump (501) is, in an embodiment, able to provide a shear rate of 2000 $s^{-1}$ inside the concentrator (2). The retentate of the concentrator (2) will subsequently be brought back to the intermediate vessel (4), whereas liquid waste will be discarded (preferably to a waste bottle, not shown on FIG. 2B). Due to the re-circulation of retentate back and forth from the intermediate vessel (4) to the concentrator (2), a heavily concentrated biomolecule product will be obtained, which can be used for further downstream processing (such as chromatographic purification) or as source for trials such as e.g. clinical trials.

The process flow from bioreactor (1) to concentrator (2) is controlled by a process controller. In order to maintain the compactness of the system, especially considering it is sized to be used inside a biosafety cabinet or isolator, the controller is integrated in a docking station (30) which is designed to receive the above-described bioreactor (1), concentrator (2) and intermediate vessel (4). The controller controls and operates bioreactor parameters as well as process flow parameters and monitors and records data from one or more sensors described above (pH, temperature and/or DO). Said controller further controls the functioning of the concentrator (2) and the recirculation of retentate from concentrator (2) to intermediate vessel (4) and back, preferably by controlling the functioning of the pump(s) (5, 501) between intermediate vessel (4) and concentrator (2).

To that purpose, said controller is provided with software allowing monitoring, controlling and recording the process flow and parameters of the system. Access to the controller can be provided to the user via a computer which is pluggable to the controller. The controller allows export of data through one or more USB connections present on said docking station and allows access to an IT network. A screen (29) such as a touch screen present on the docking station allows the user to follow the process flow and measured parameters as well as to manually operate the system, e.g. by starting or stopping certain sub-processes.

As described above, the docking station (30) with integrated controller further allows for docking of a bottle for supply of base (13) to the bioreactor (1). Such bottle may be a PET bottle, with a volume of between 500 mL to 5000 ml. Said docking station (30) may further allow docking of a bottle for supply of inoculum (10)/additive (not shown) to the bioreactor (1). A retention tray for catching potential liquid overflows can be provided.

The docking station (30) will be preferably constructed out of a material that allows cleaning with a NaOH (such as 0.5 M NaOH) solution, alcohols such as ethanol or virucides such as Virkon. The docking station (30) should equally be able to resist a sterilizing regime using vaporized hydrogen peroxide (VHP). In a preferred embodiment, the material of said docking station (30) is a corrosion resistant metal. The docking station (30) can be powered by a power supply, such as a standard 110-230V, 50-60 Hz power supply.

Figure 3:
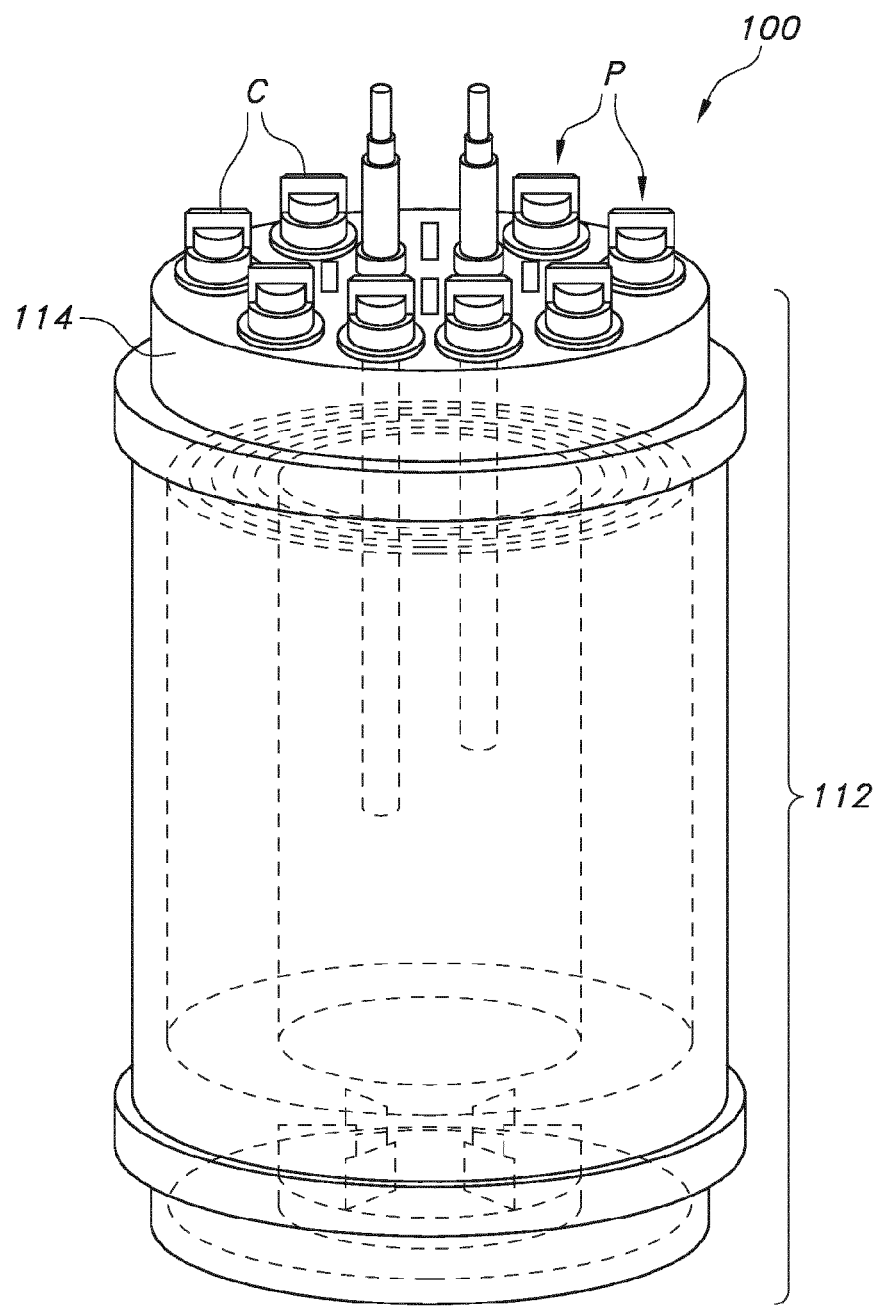
FIG. 3 is a perspective view of a first embodiment of a bioreactor according to the disclosure.
Figure 4:
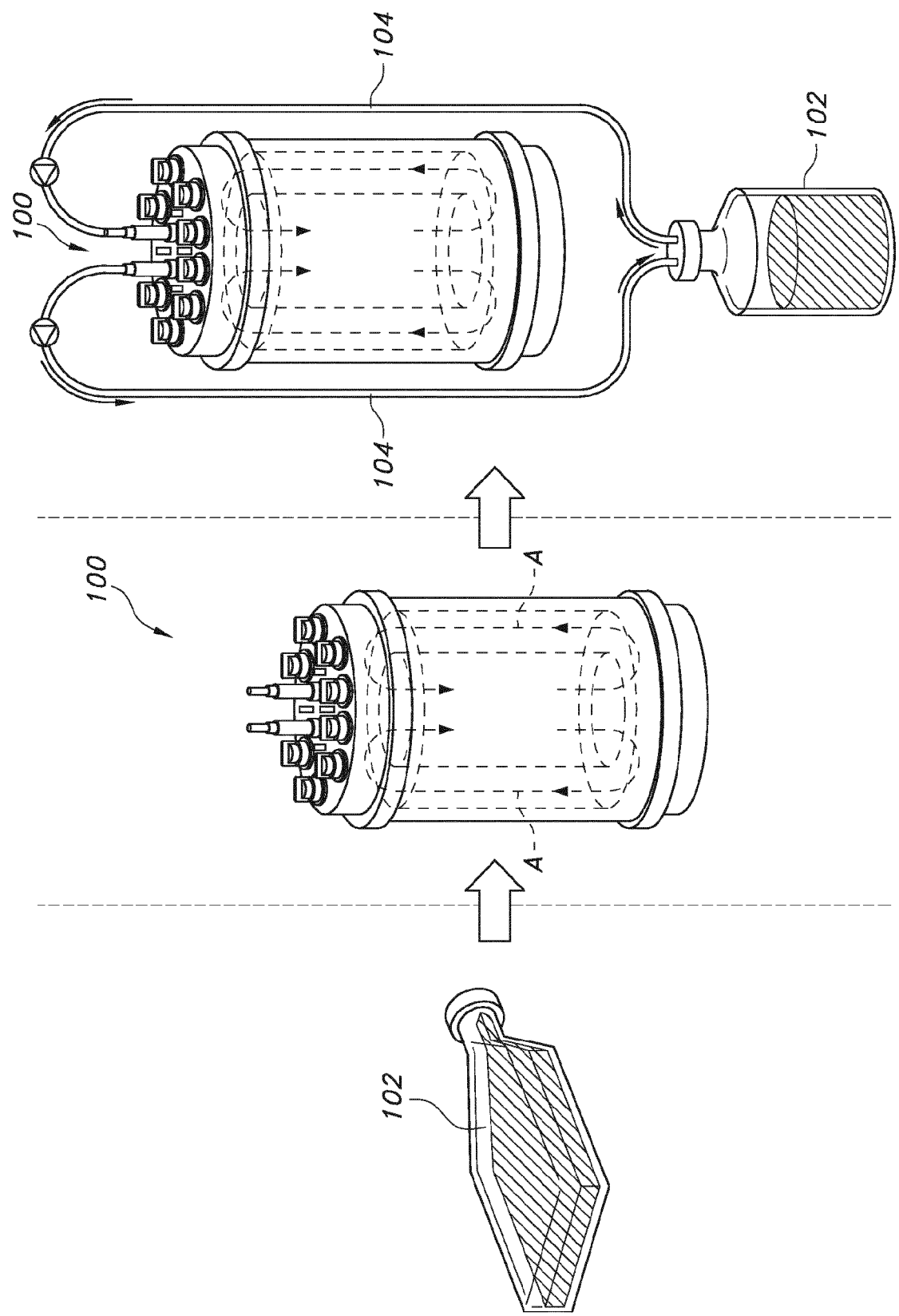
Figure 5:
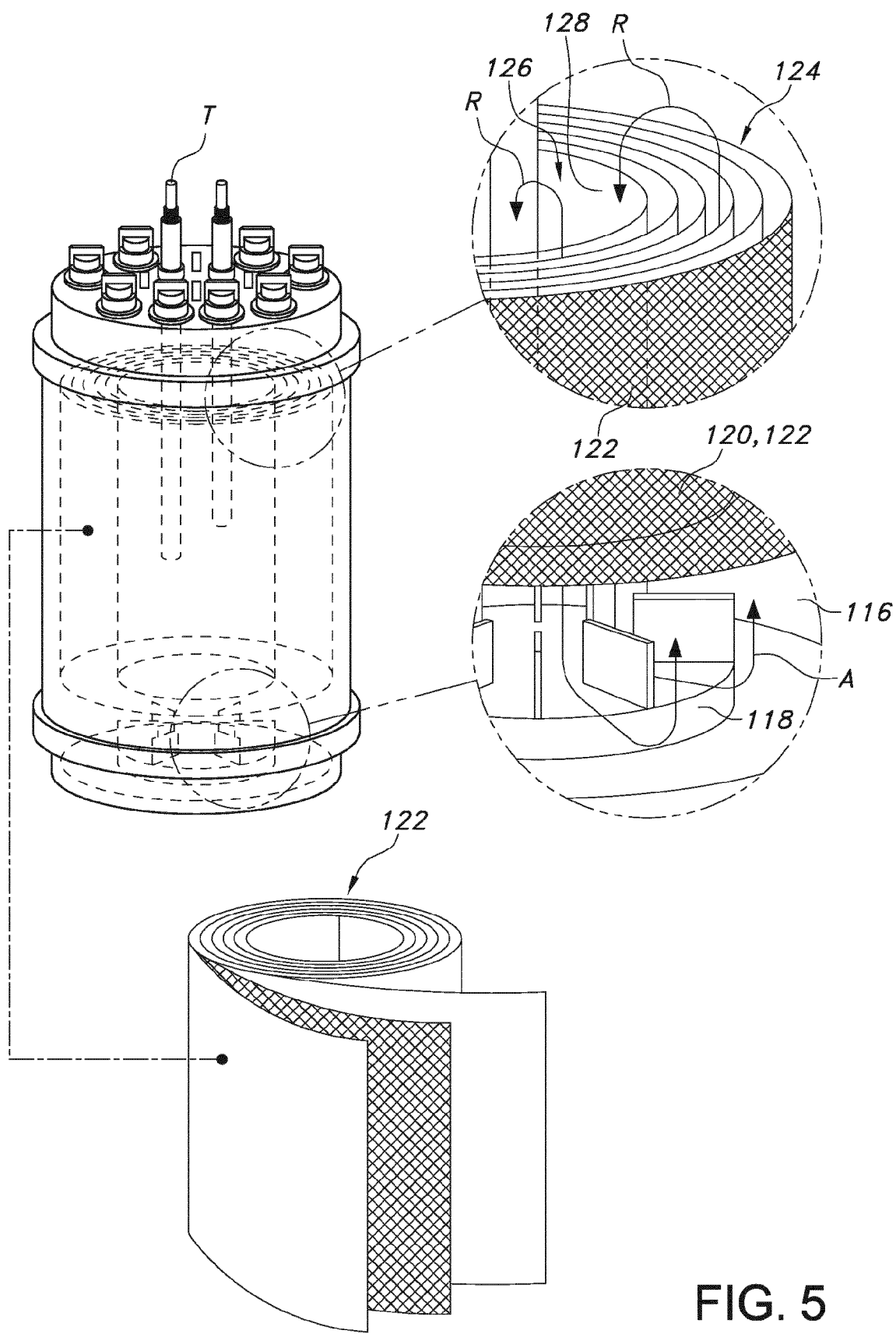
FIG. 5 is a perspective view of the bioreactor of FIG. 1, including several enlarged views.

Reference is now made to FIGS. 3-5, which illustrate one embodiment of a bioreactor 100 for culturing cells, according to one aspect of the disclosure. In some embodiments, the bioreactor 100 includes an external casing or housing 112 forming an interior compartment and a removable cover 114 for covering the interior compartment, which may include various openings or ports P with removable covers or caps C for allowing for the selective introduction or removal of fluid, gas (including by way of a sparger), probes, sensors, samplers, or the like. As indicated in FIGS. 2, 2A, and 2B, in some embodiments, the bioreactor 100 may be used in connection with an external reservoir 102 and conduits 104 (e.g., forward and return) to form a continuous loop for circulating fluid to the bioreactor 100.

Figure 6:
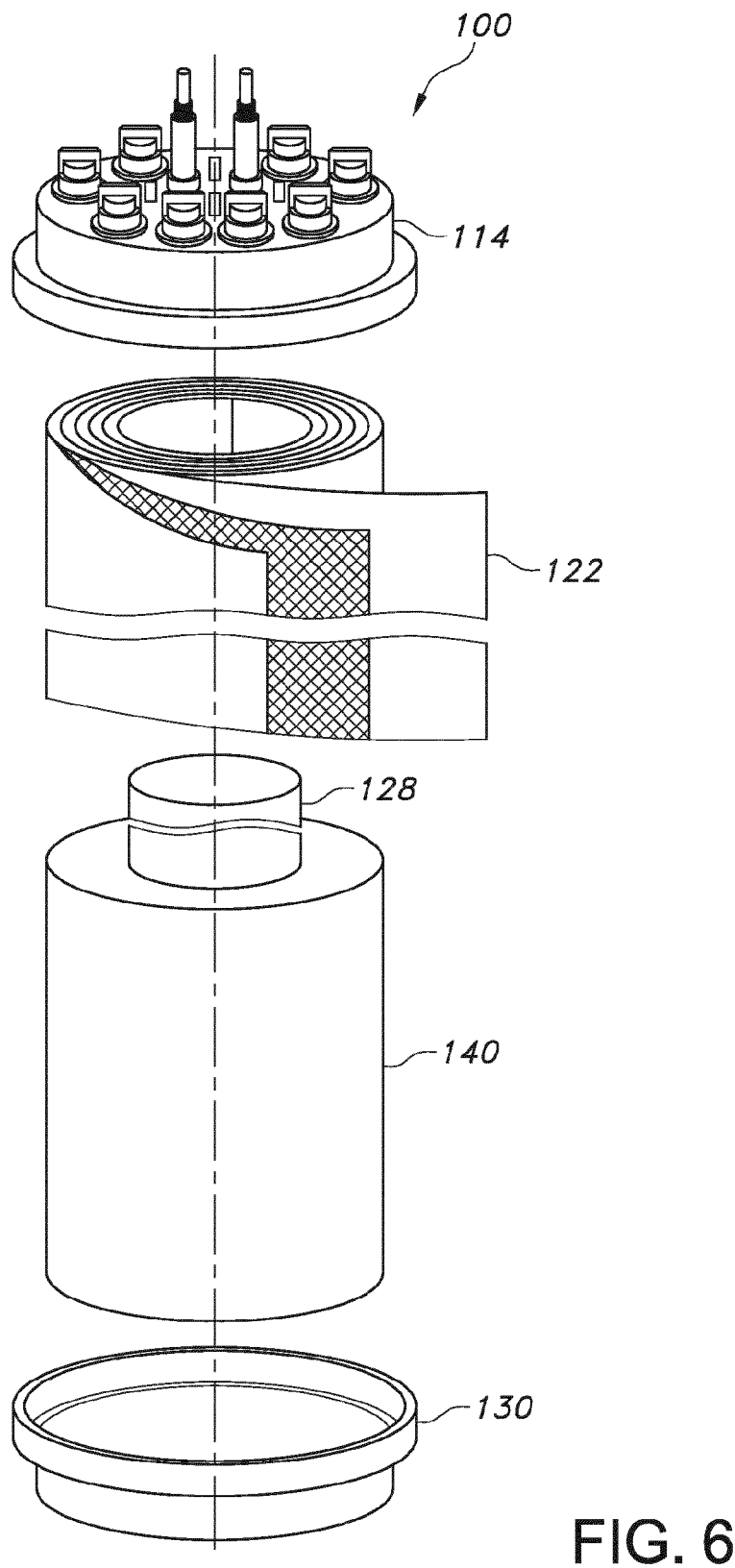
FIG. 6 illustrates a modular version of the bioreactor of FIG. 3.

Within the interior compartment formed by the bioreactor housing 112, several compartments or chambers may be provided for transmitting a flow of fluid or gasses throughout the bioreactor 100. As indicated in FIG. 5, in some embodiments, the chambers may include a first chamber 116 at or near a base of the bioreactor 100. In some embodiments, the first chamber 116 may include an agitator for causing fluid flow within the bioreactor 100. In some embodiment, the agitator may be in the form of a "drop-in" rotatable, non-contact magnetic impeller 118 (which as outlined further below may be captured or contained within a container (not shown) including a plurality of openings for admitting and releasing fluid). In some embodiments, as a result of the agitation provided, fluid may then flow upwardly (as indicated by arrows A in FIG. 6) into an annular chamber 120 along the outer or peripheral portion of the bioreactor 100. In some embodiments, the bioreactor is adapted to receive a fixed bed, such as a structured spiral bed 122, which in use may contain and retain cells being grown. As indicated in FIG. 5, in some embodiments, the spiral bed 122 may be in the form of a cartridge that may be dropped or placed into the chamber 120 at the point of use. In some embodiments, the spiral bed 122 can be pre-installed in the chamber during manufacture at a facility prior to shipping.

In some embodiments, fluid exiting the chamber 120 is passed to a chamber 124 on one (upper) side of the bed 122, where the fluid is exposed to a gas (such as oxygen or nitrogen). In some embodiments, fluid may then flow radially inwardly to a central return chamber 126. In some embodiments, the central return chamber can be columnar in nature and may be formed by an imperforate conduit or tube 128 or rather formed by the central opening of the structured spiral bed. In some embodiments, the chamber 126 returns the fluid to the first chamber 116 (return arrow R) for recirculation through the bioreactor 100, such that a continuous loop results ("bottom to top" in this version). In some embodiments, a sensor, for example a temperature probe or sensor T may also be provided for sensing the temperature of the fluid in the chamber 126. In some embodiments, additional sensors (such as, for example, pH, oxygen, dissolved oxygen, temperature) may also be provided at a location before the fluid enters (or re-enters) the chamber 116. The sensors and probes as described herein, may be reusable, one-time-use and/or disposable.

Figure 5A:
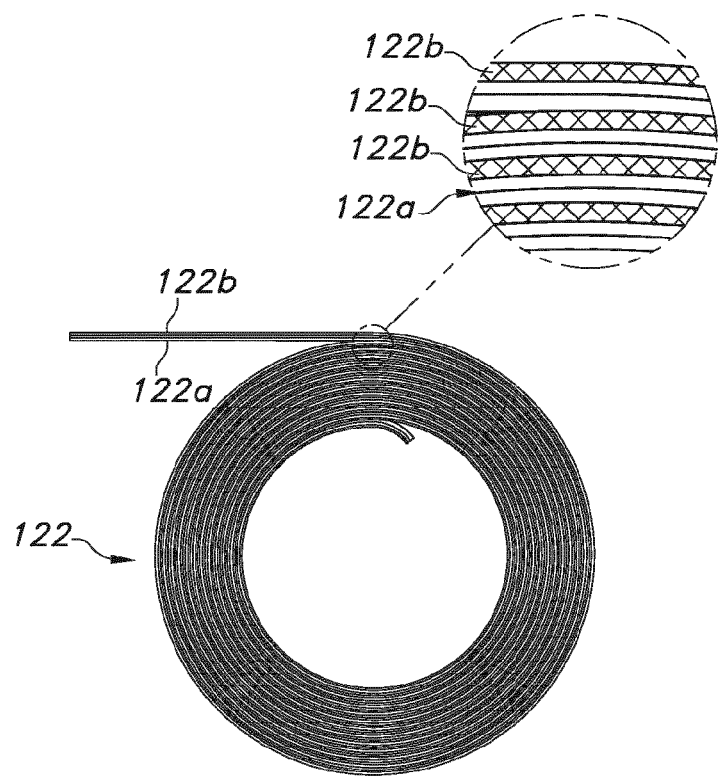
FIGS. 5A, 5B and 5C illustrate a matrix material for use in forming a structured fixed bed for culturing cells in any of the disclosed bioreactors.
Figure 5B:
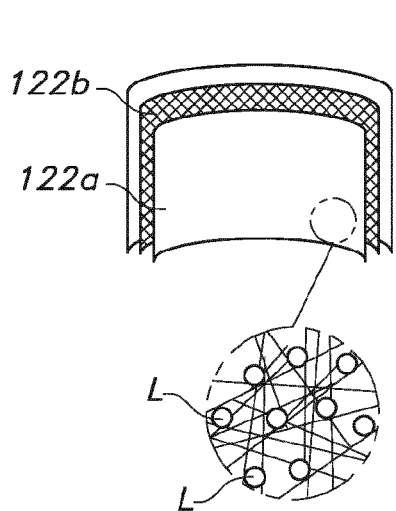
Figure 5C:
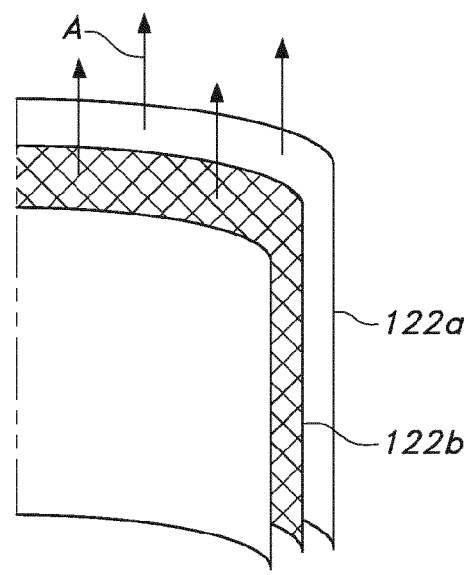

FIG. 5A shows one embodiment of a matrix material for use as a structured fixed bed in the bioreactor of the present disclosure and, in particular, a spiral bed 122. In some embodiments, one or more cell immobilization layers 122a are provided adjacent to one or more spacer layers 122b made from a mesh structure. In some embodiments, the layering may optionally be repeated several times to achieve a stacked or layered configuration. In some embodiments, the mesh structure included in spacer layers 122b forms a tortuous path for cells (see cells L in FIG. 5B suspended or entrapped in the material of the immobilization layer 122a), and a cell culture may form part of any invention claimed herein) and fluid to flow when layered between two immobilization layers 122a. Homogeneity of the cells is maintained within the structured fixed bed as a result of this type of arrangement. In some embodiments, other spacer structures can be used which form such tortuous paths. In some embodiments, as shown in FIG. 5A, the structured fixed bed can be subsequently spirally or concentrically rolled along an axis or core (e.g., conduit 128, which may be provided in multiple component parts). In some embodiments, the layers of the structured fixed bed are firmly wound. In some embodiments, the diameter of the core, the length and/or amount of the layers will ultimately define the size of the assembly or matrix. In some embodiments, thickness of each of the layers 122a, 122b may be between 0.1 and 5 mm, 01 and 10 mm, or 0.001 and 15 mm.

Figure 8:
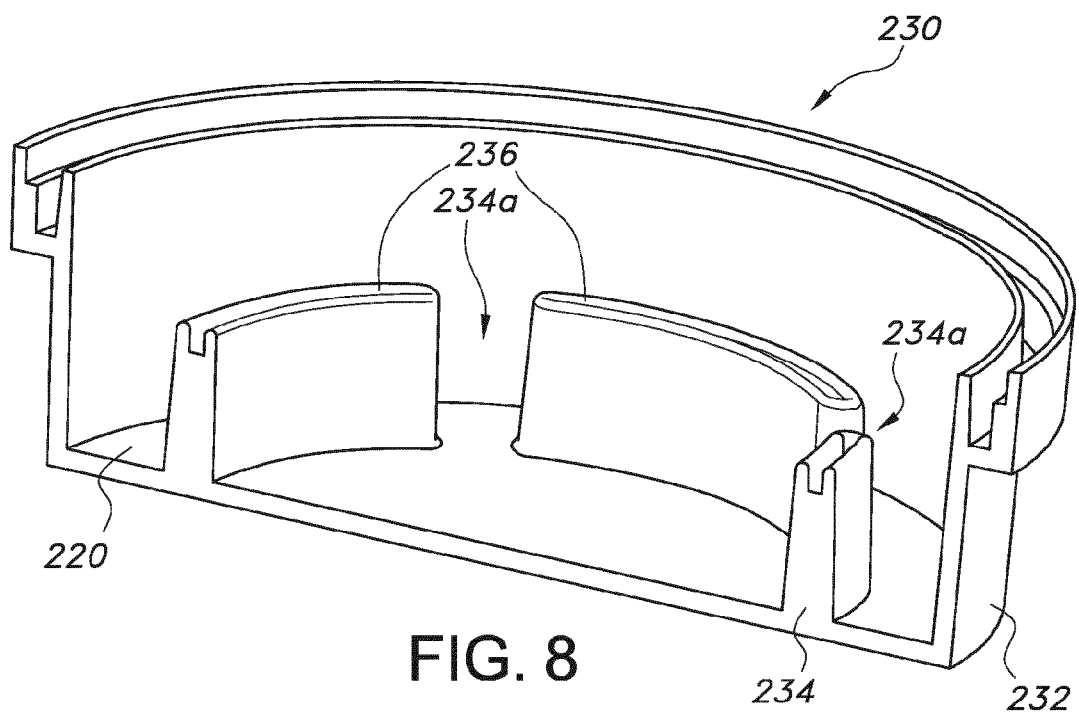
FIG. 8 is a cross-sectional view of a base portion of the bioreactor of FIG. 7.
Figure 9:
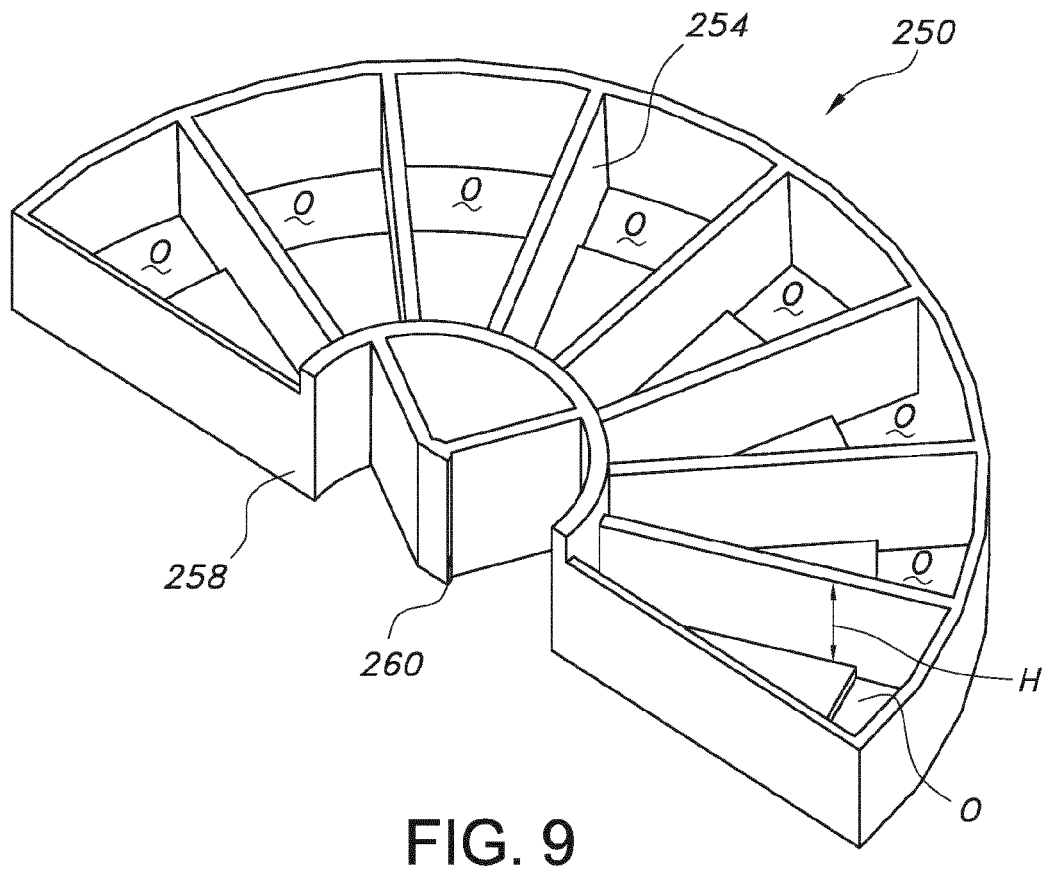
FIG. 9 is a partially cutaway top view of an intermediate part of the bioreactor of FIG. 7.

According to one aspect of this disclosure, the bioreactor 100 in certain embodiments may be "modular." In some embodiments, a modular bioreactor can be comprised of a plurality of discrete modules that interact together to create a space suitable for culturing cells in a manner that is highly predictive due to the manufacturing homogeneity of the modules. In some embodiments, a modular bioreactor is not limited to particular shape or form (e.g., cylindrical or otherwise, and with a structured fixed bed or unstructured bed, depending on the application). For example, as shown in FIG. 8, In some embodiments, the modules may comprise a base portion formed by base module 130, an intermediate portion formed by an intermediate module 140 (which may be formed from a number of stackable modular portions, as outlined further in the description that follows), an optional associated central module, such as conduit or tube 128, which may also be considered part of the intermediate module, and a cover module, such as formed by a cover part in the form of lid or removable cover 114. In some embodiments, the modules may be separately manufactured as individual components and either assembled at a manufacturing facility based on an intended application (and then shipped to a point of use) or assembled based on an intended application at the point of end use. In some embodiments, the modules of the bioreactor 100 interact to create a place for growing cells, such as in a high-density manner using a fixed bed, such as for example a structured or unstructured fixed bed.

A further embodiment of a bioreactor 200 according to the disclosure is shown in FIGS. 7-11. In some embodiments, the bioreactor (whether modular or otherwise pre-assembled as a single unit) can comprise a base, an intermediate portion and a cover. In some embodiments, a base portion can comprise a base part 230. In some embodiments, an intermediate portion can comprise intermediate parts 250 and/or 270. In some embodiments, intermediate parts 250 and 270 are not identical. In some embodiments, a cover portion can comprise a cover part 280. Referring to FIG. 8, in some embodiments, base part 230 may include an external wall 232 and an internal wall 234, which may define a first chamber 216 for receiving the agitator (not shown). In some embodiments, the internal wall 234 can include openings 234a for allowing fluid flow to the second, radially outward chamber 220 bounded by the external or outer wall 232.

Figure 7:
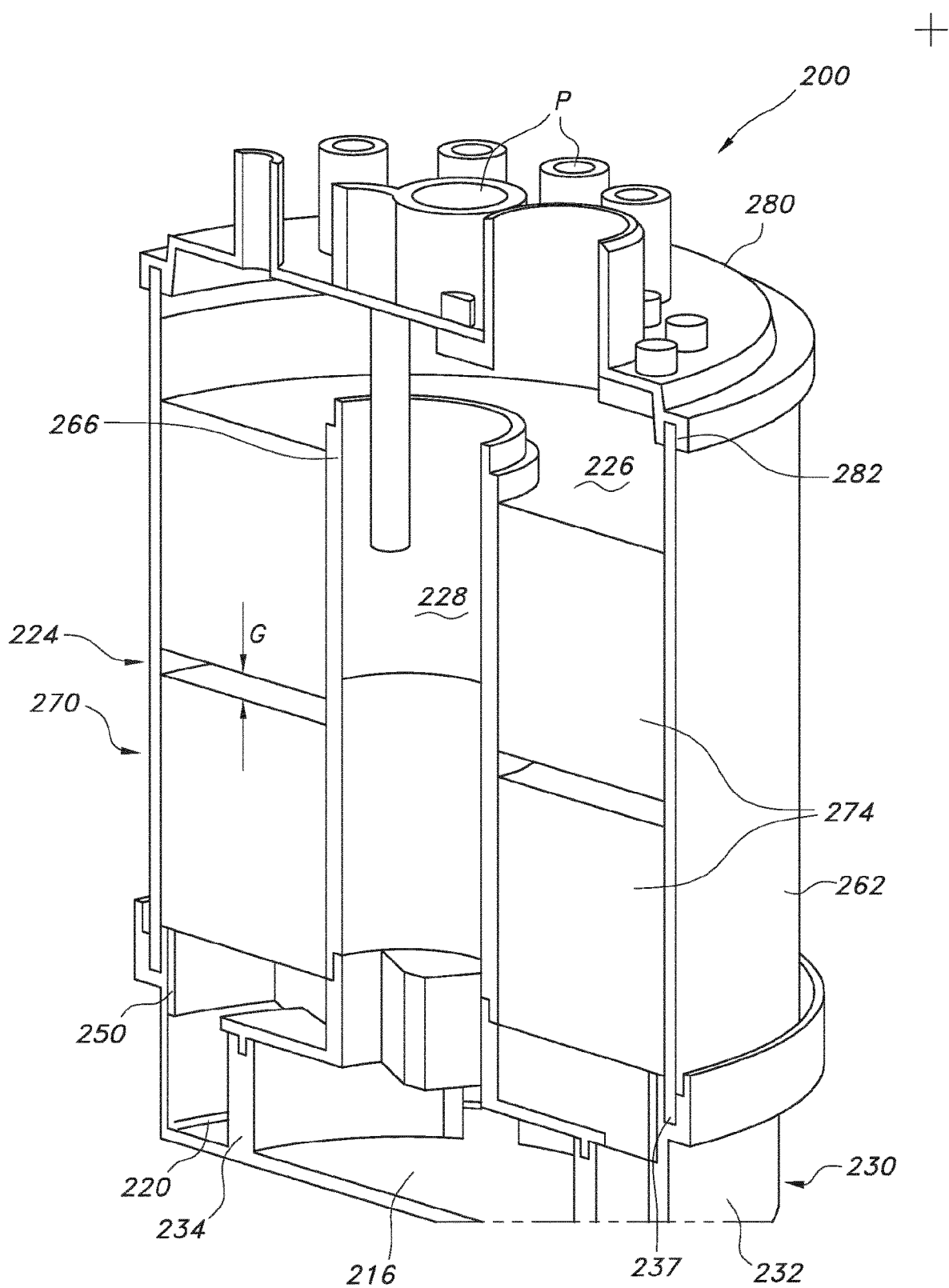
FIG. 7 is a cross-sectional view of a second embodiment of a bioreactor according to the disclosure.
Figure 10:
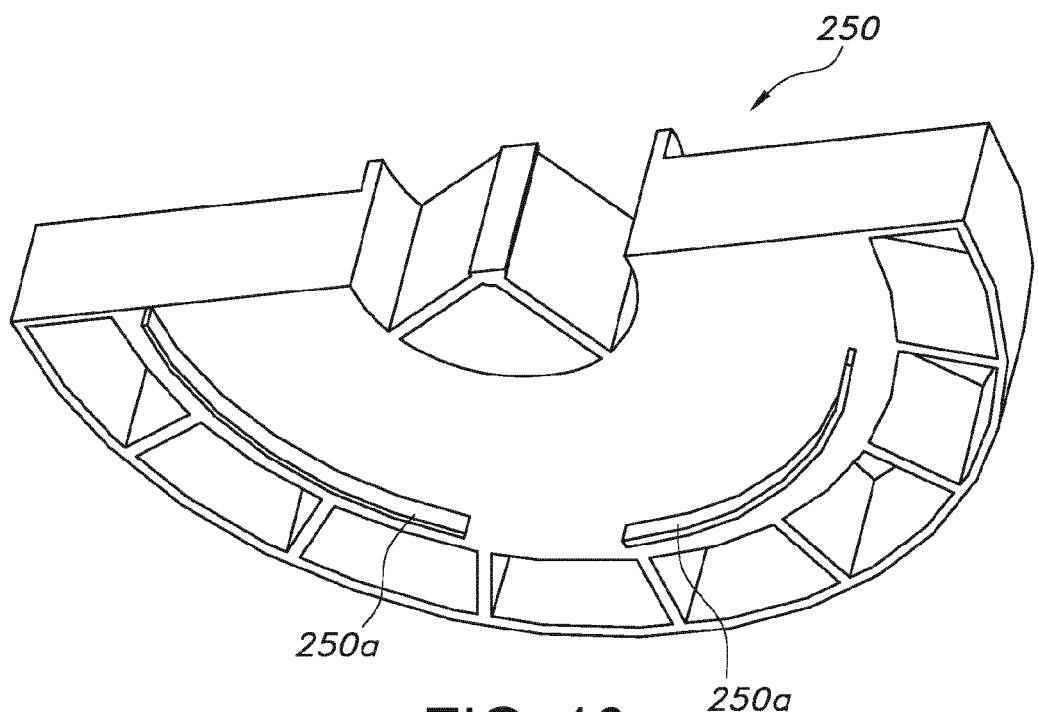
FIG. 10 is a partially cutaway bottom view of an intermediate part of the bioreactor of FIG. 7.
Figure 11:
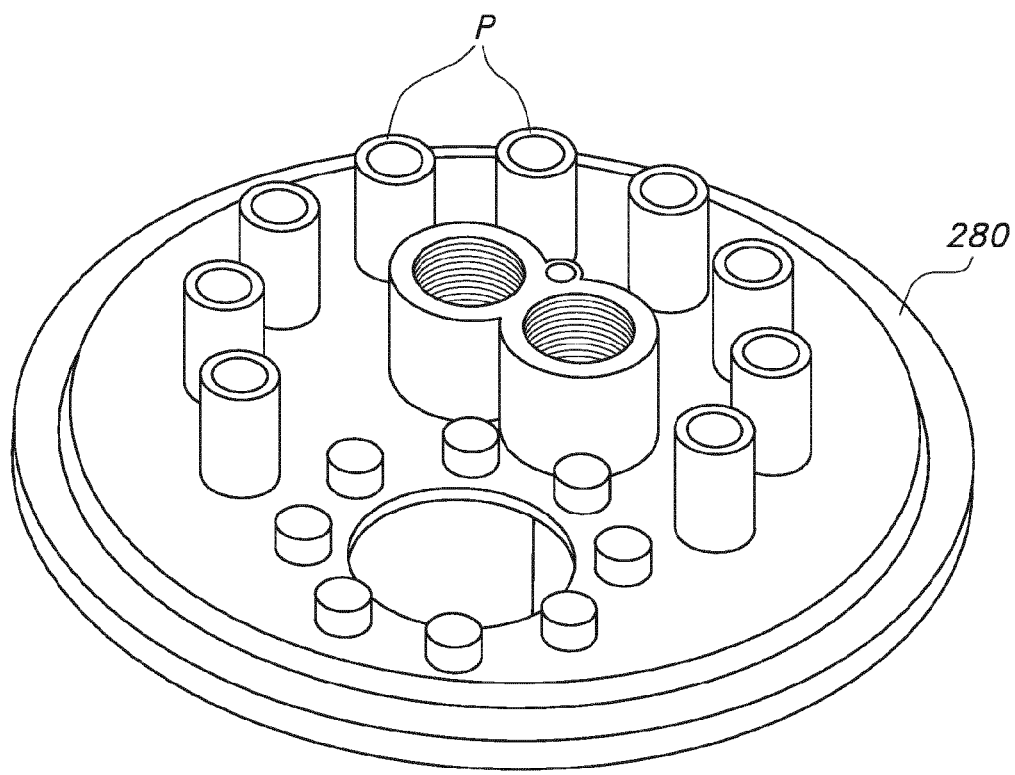
FIG. 11 is a perspective view of a cover portion of the bioreactor of FIG. 7.

As can be seen in FIG. 8, in some embodiments, the internal wall 234 may include a plurality of connectors, such as grooves 236, for engaging corresponding connectors, such as tongues 250a, on the first intermediate part 250, as shown in FIG. 10. In some embodiments, the internal wall 234 may be of lower/higher height than the external wall 232. In some embodiments, the internal wall 234 may be of lower height than the external wall 232, as can be seen in FIG. 8. With reference to FIG. 7, in some embodiments, the first intermediate part 250 may be at least partially recessed within the base part 230.

In some embodiments, the base part 230 may include a peripheral connector, such as a groove 237. In some embodiments, the connector or groove 237 can be adapted to receive a corresponding connector of a second intermediate part 270, which may simply be part of an outer wall 262 thereof. In some embodiments, within the intermediate part 270 can be located a plurality of fixed beds 274 in a third chamber 224 (but a single monolithic fixed bed could be used, which in this or any disclosed embodiment may take any size, shape, or form), which could be supported by an interposed support, but a gap G could also be provided between adjacent sections of fixed beds). The gap could also be eliminated, such that an upper bed rests on and is supported by a lower one.

In some embodiments, the structured fixed bed can be of the spiral form, as shown in FIGS. 5, 5A, 5B, and 5C (which spiral form can be implemented in any embodiment of a bioreactor, disclosed or otherwise). In the case of a spiral bed, the bed may be wound around an internal wall 266, which may form a fifth chamber 228 for returning fluid to the first chamber 216 in the base part 230. The internal wall 266 may comprise multiple stacked tubular parts, as shown. In some embodiments, the multiple stacked tubular parts can allow for the height to be adjusted depending on the number of fixed beds present (e.g., one tubular part may be provided for each stacked bed).

In some embodiments, the cover part 280, or lid can be adapted to removably connect with the second intermediate part 270, and thus form a fourth chamber 226 in which the liquid encounters gas, for example air. In some embodiments, the connection between the cover part and the second intermediate can be by a connector, such as a groove 282, which receives the upper end of the outer wall 262 or any access mechanism disclosed herein. The lid or cover part 280 may include various ports P.

Turning back to FIGS. 9 and 11, further details of the intermediate part 250 are shown. In some embodiments, part 250 may include a plurality of radially extending supports 254, which thus lend support for a structured fixed bed when resting thereon in the adjacent third chamber 224. In some embodiments, supports 254 may also support a lower shelf 256 defining a partial opening O for allowing fluid to flow vertically. In some embodiments, the height H of the supports 254 can be sufficient to allow the fluid to develop sufficient upward velocity before entering the chamber 224 to pass through the full section of the fixed bed 274.

In some embodiments, an inner annular wall 258 can be connected to the inboard end of the supports 254. In some embodiments, the wall 258, corresponds in diameter to the diameter of the internal wall 266 of the intermediate part 270, which may also connect with it (such as by nesting). In some embodiments, the internal wall 266 can form a passage for delivering fluid from the fifth chamber 228 to the first chamber 216. In some embodiments, a flow disruptor 260 may be provided in this passage to help prevent the creation of any vortex within the fifth chamber 228.

Figure 12:
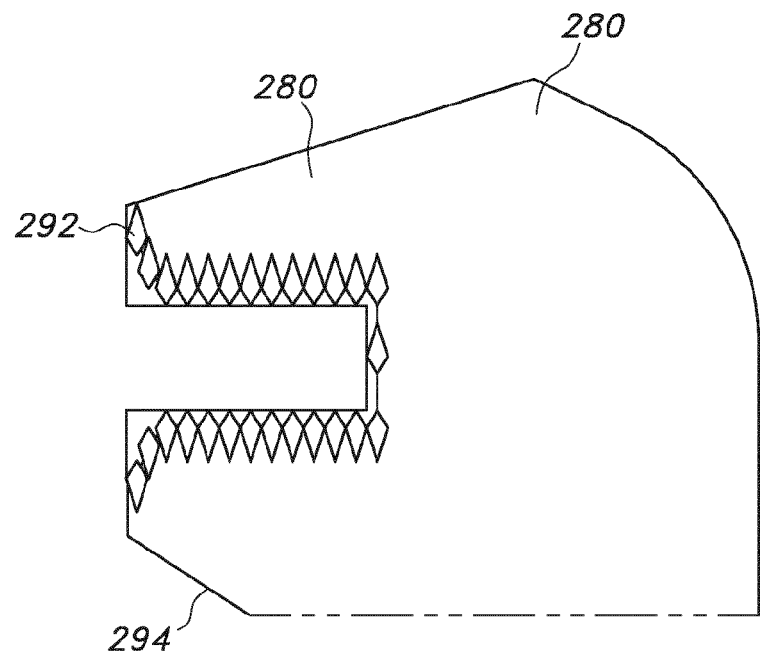
FIG. 12 is a cross-sectional view of a manner of providing metal threads in a plastic port.

In some embodiments, it may be desirable to provide one or more of the ports P on the cover part 280 with internal threading in order to establish a threaded connection with a component, such as a sensor (not shown). Thus, according to a further aspect of the disclosure, and with reference to FIGS. 11 and 12, the cover part 280 may be formed by providing a metal insert 292 with a helical thread into an injection mold 294, and then injecting a plastic material into the mold to form a composite part. In some embodiments, the threads may be reliably provided in the cover part 280, which may otherwise be formed of plastic. As can be appreciated, this technique may also be used in connection with any other parts of the disclosed bioreactors requiring threaded fittings or ports. In some embodiments, inserts for use in this technique may be obtained from Wilhelm Bollhoff GmbH & Co. KG of Bielefeld, Germany, under the IMTEC brand.

From FIG. 7, in some embodiments, it can be understood that the flow from one fixed bed module to the next-adjacent fixed bed module in the cell culturing chamber 224 can be direct or uninterrupted. In some embodiments, the outer chamber 224 can create a continuous flow path through the multiple beds located therein, which may be structured fixed beds, unstructured fixed beds, or unstructured beds. In some embodiments, the continuous and substantially unimpeded flow through the predesigned and matching bed modules helps to promote homogeneity for cell growth and other processing and enhances the consistency of the cell culturing operation, and also promotes the ability to take measurements or samples from the stacked beds, which is not readily possible if blocking partitions (as contrasted with the perforated supports, as discussed below) are present. Finally, in a structured bed embodiment, the manufacture of the overall bioreactor is even less complicated and labor intensive as the effort to match the properties and characteristics from one fixed bed module to the other is greatly reduced.

Figure 13:
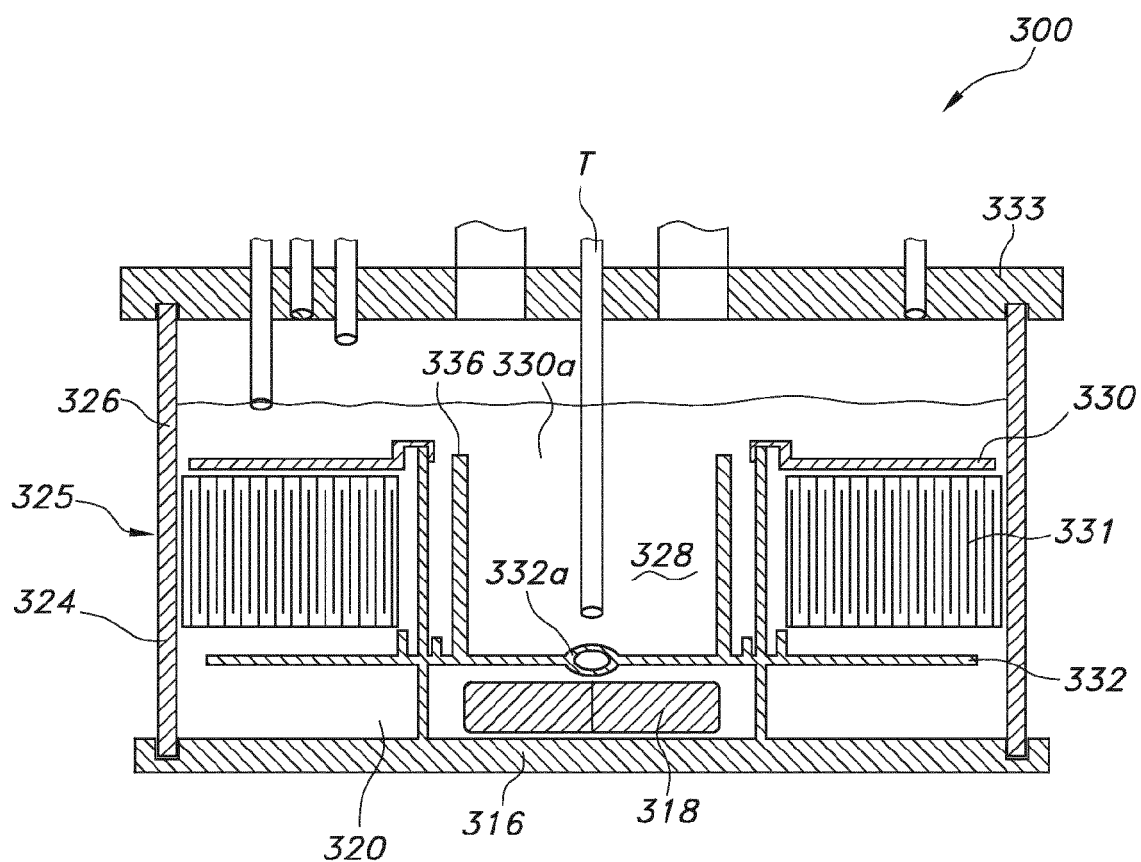
FIGS. 13, 13A and 13B are various view of a third embodiment of a bioreactor according to the disclosure.
Figure 13A:
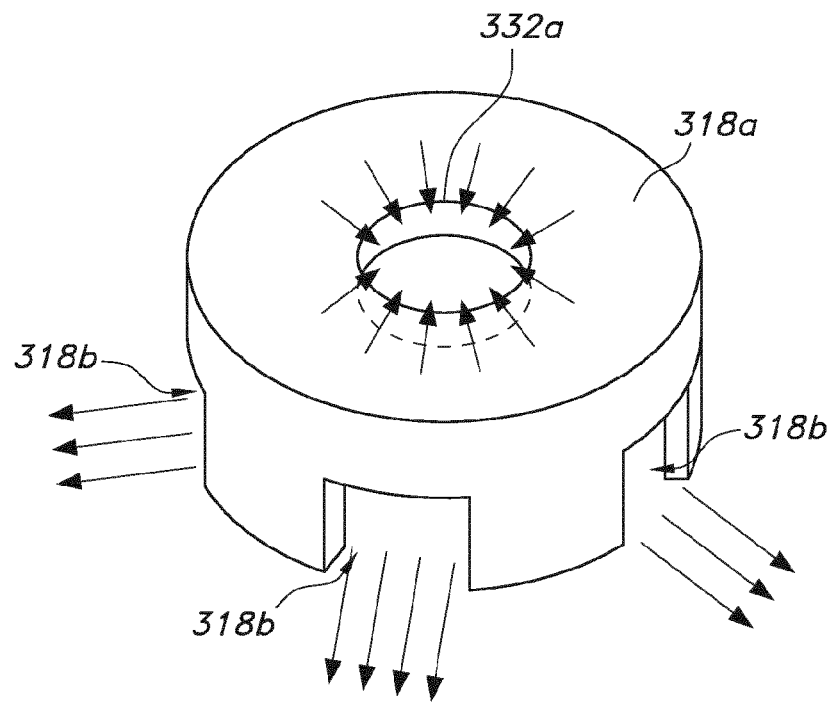
Figure 14:
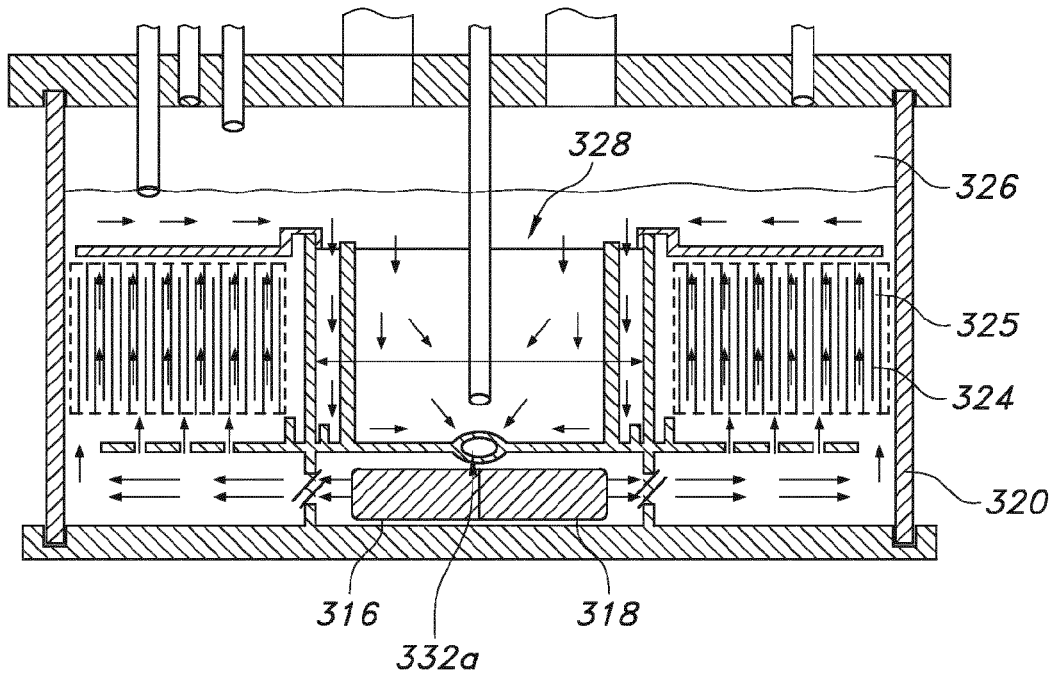
FIG. 14 is a cross-sectional view of the bioreactor of FIG. 13.

Reference is now made to FIGS. 13 and 14, which schematically illustrate a third embodiment of a bioreactor 300, which for purposes of clarity is shown in cross-section. In some embodiments, the bioreactor 300 (whether modular or otherwise pre-assembled as a single unit) comprises an external housing 331 with a cover 333, either of which may include various openings or ports for allowing for fluid introduction or removal. In some embodiments, within the bioreactor housing 331, several compartments or chambers are provided, including a first chamber 316 including an agitator for causing fluid flow within the bioreactor 300, which may be in the form of a "drop-in" rotatable, non-contact magnetic impeller 318 or an agitator disclosed herein. As indicated in FIG. 13A, in some embodiments, the impeller 318 may be housed, captured or contained within a housing, such as a housing or container 318a including a plurality of openings 318b serving as inlets and outlets for admitting and releasing fluid (but any other form of agitator could be used). In some embodiments, the agitation created may be such that fluid is caused to flow into a second or outboard annular chamber 320, which is radially outward of the first chamber 316.

In some embodiments, fluid may then flow upwardly (as indicated by arrows in FIG. 14) into a third annular chamber 324 along an intermediate, outer portion of the bioreactor 300. In some embodiments, the outer portion can be adapted to receive a fixed bed, such as a structured spiral bed 325, but other forms may be used), which in use may contain cells being grown. In some embodiments, the spiral bed 325 may be in the form of a cartridge that may simply be dropped into the chamber 324 at the point of use, or could be pre-installed in the chamber during manufacture at a facility prior to shipping.

In some embodiments, fluid exiting the third chamber 324 can then passed to a fourth chamber 326, where it is exposed to a gas (such as air) and then flows radially inwardly to a fifth chamber 328, which is columnar in nature and returns the fluid to the first chamber 316 for recirculation through the bioreactor 310, such that a continuous loop results. In some embodiments, a temperature probe or sensor T, or any other sensor disclosed herein may also be provided for sensing a parameter, for example the temperature of the fluid directly in the fifth chamber, and additional sensors (such as, for example, pH or dissolved oxygen) may also be provided at this location (which is before the fluid enters (or re-enters) the fixed bed 325).

Figure 13B:
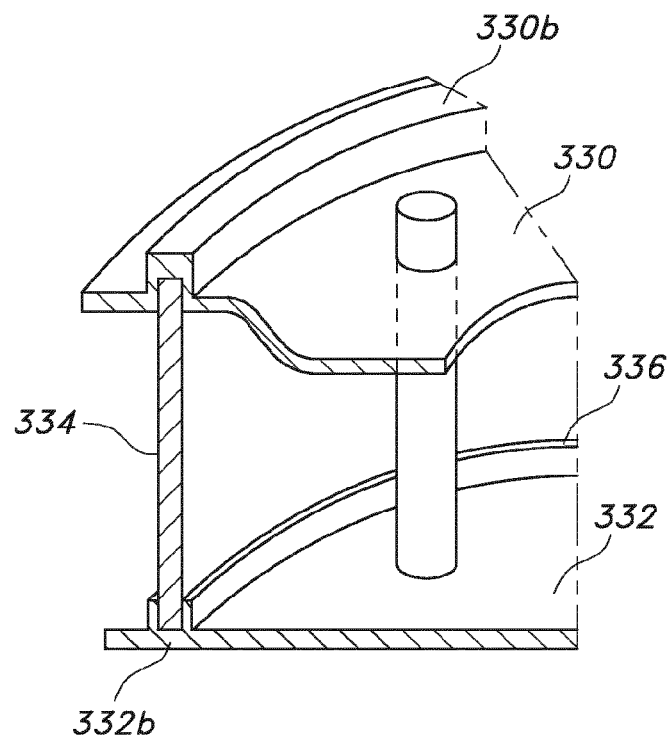

From the partially cutaway image at FIG. 13B, it can be understood that the third chamber 324 may be bounded by upper and lower plates 330, 332, which include openings or perforations for allowing fluid generally free of cells to enter and exit the fixed bed 325. In some embodiments, the lower plate 332 may include a central opening 332a for allowing fluid to pass from the fifth chamber 328 to the first chamber 316 for recirculation. In some embodiments, the upper plate 330 can include an opening 330a, into which fluid may travel to enter the fifth or return chamber 328.

In some embodiments, support for the upper plate 330 may be provided by a hollow, generally cylindrical tube 334, but could take other shapes. In some embodiments, the opposed ends of this tube 334 may fit into corresponding grooves 330b, 332b in the plates 330, 332 (in some cases the lower plate 332 can be integral with the impeller housing or container 318a in the illustrated embodiment). In some embodiments, supports, such as generally vertical rods 336, can be arranged to provide added support for the plate 330. In some embodiments, the disclosed vertical rods 336 do not interfere in any significant way with the fluid flow in the corresponding chamber 328. In some embodiments, the ends of the rods 336 may be recessed in the plates 330, 332, or held in place by suitable fasteners or locking mechanisms (e.g., locking connections, bolts or adhesives).

From FIG. 14 and the action arrows provided thereon, it can be understood that, as a result of the fluid agitation, in some embodiments, fluid may flow from the chamber 316 outwardly into chamber 320. In some embodiments, the fluid can then be redirected to pass vertically through chamber 324 including the fixed bed, and into chamber 328. In some embodiments, fluid is then directed inwardly to chamber 328, where the fluid may return to the first chamber 316 via opening 332a. In some embodiments, fluid can refer to culture medium.

Figure 15:
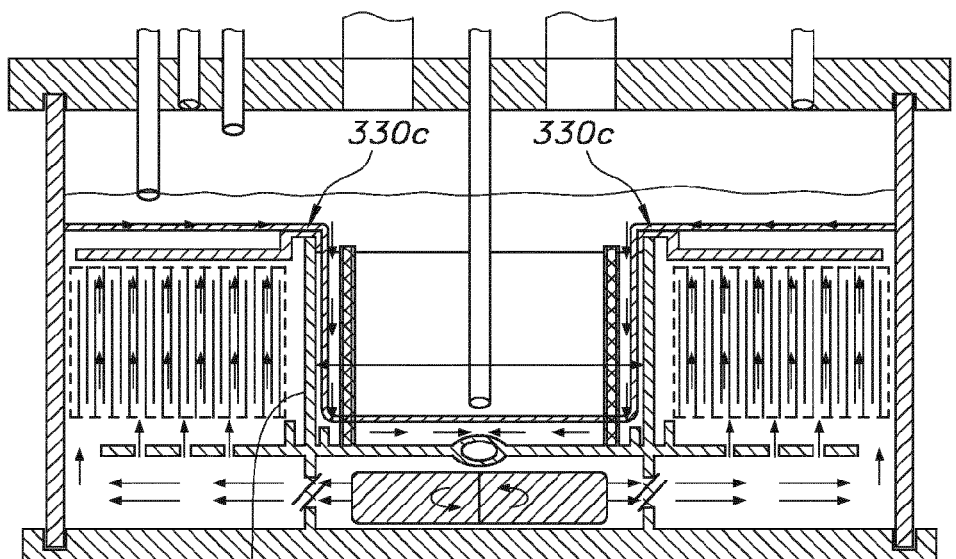
FIG. 15 is cross-sectional view of the bioreactor of FIG. 13.

FIG. 15 further illustrates an arrangement in which, in some embodiments, the upper plate 330 is provided with peripheral openings 330c to allow fluid to flow directly along the inner wall formed by tube 334. In this manner, a thin layer or film of fluid may be created, which flows downwardly while passing through the fifth chamber 328. In some embodiments, this may serve to increase the volume of the fluid exposed to gas (air) within the fifth chamber 328, prior to it being returned to the first chamber 316. In some embodiments, this implementation can allow for more oxygen transfer which may be needed for larger sizes or otherwise to increase cell growth rates adjust process parameters based on the biologic being produced.

In some embodiments, the "waterfall" implementation that creates a fluid film can be achieved by adding a limited quantity of cell culture medium from the start, such that only a small overflow results. Alternatively, in some embodiments, the "waterfall" implementation is achieved by adding cell culture medium and cells and then when cells are growing in the bed, withdraw culture medium (such as using a dip tube) in the corresponding chamber, such as chamber 328.

In some embodiments, a fourth embodiment of a bioreactor 400 is described with reference to FIGS. 16-18. In this embodiment, the bioreactor 400 includes the first through fifth chambers 416, 420, 424, 426, and 428 as noted above (fixed bed not shown), but the housing 412 is comprised of a plurality of modular parts. In some embodiments, the parts include a base part 430, one or more intermediate parts 450, and a cover part 470. In some embodiments, the parts 430, 450, 470 can be adapted to interact in a fluid-tight manner so as to form the bioreactor 400 with the chambers 416, 420, 424, 426, and 428, as noted.

Figure 16:
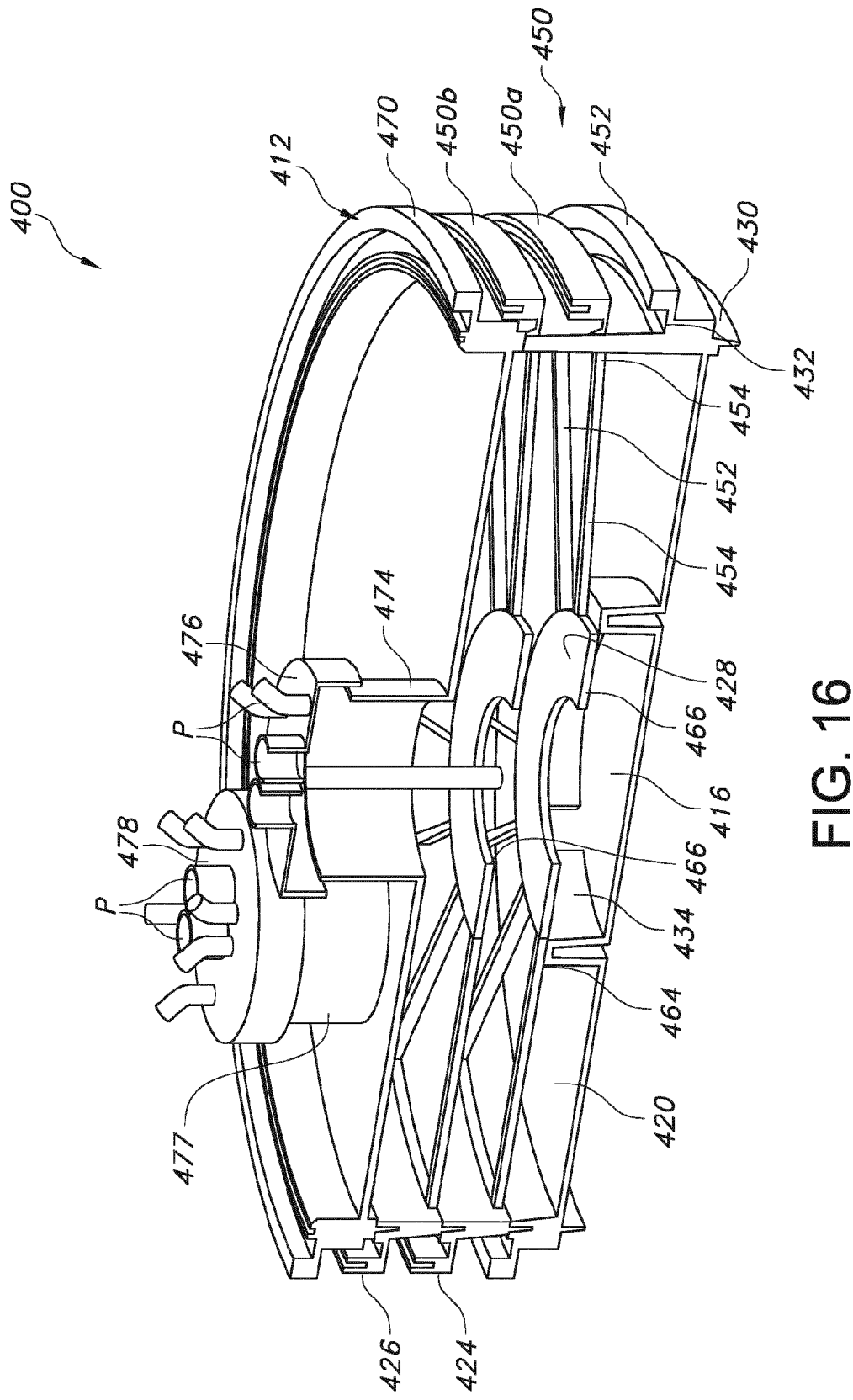
FIG. 16 is a cross-sectional view of a fourth embodiment of a bioreactor according to the disclosure.
Figure 17:
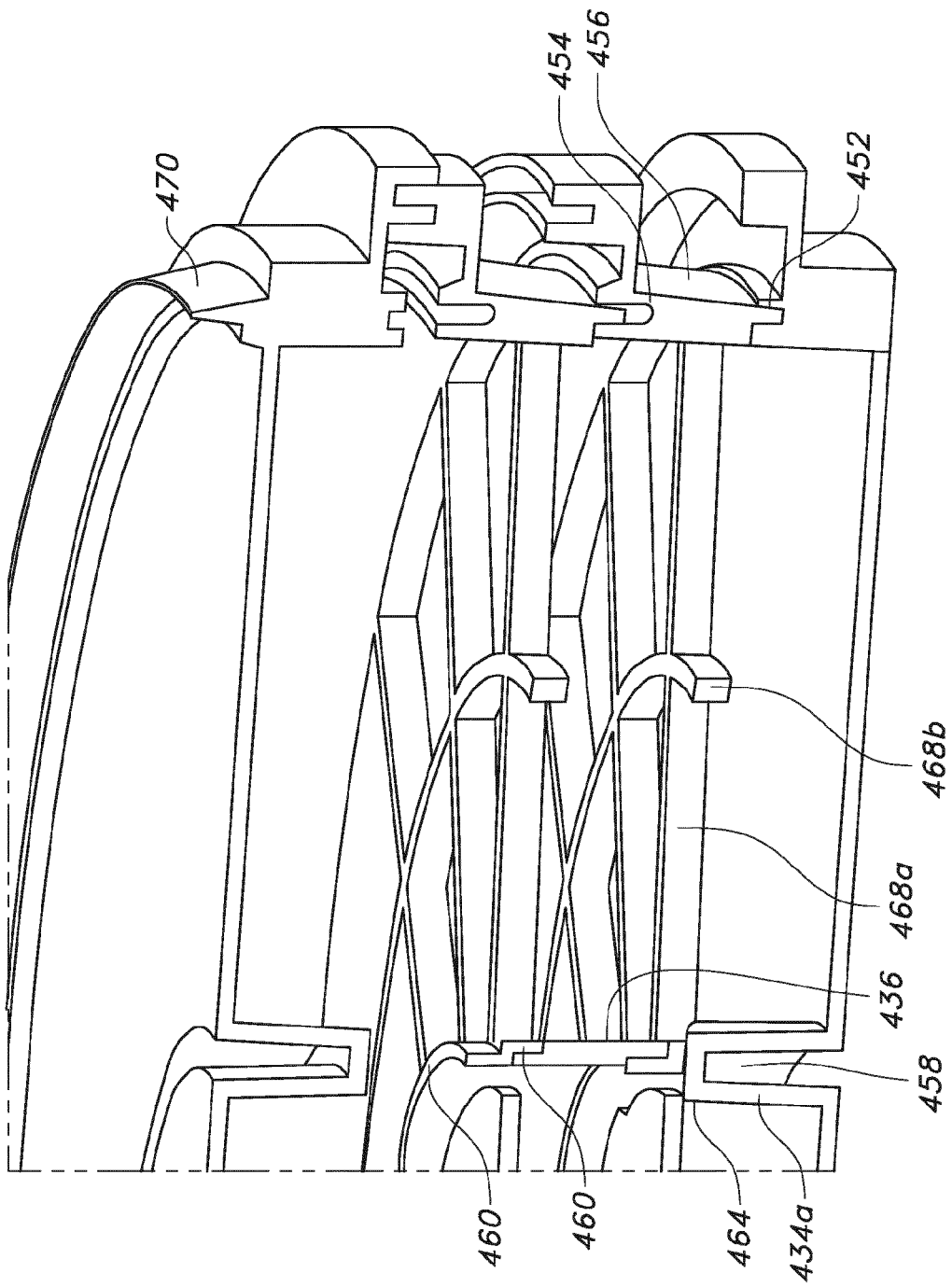
FIG. 17 is a partially cutaway view of a portion of the bioreactor of FIG. 16.

In some embodiments, and as perhaps best understood from FIG. 16, the base part 430 can include a peripheral connector, shown in the form of a groove 432, for receiving and engaging a corresponding peripheral connector, such as a tongue 452, projecting from one of the intermediate parts 450. In some embodiments, interiorly, the base part 430 can include an upstanding wall 434, which defines the first chamber 416 for receiving a fluid agitator (not shown). In some embodiments, the wall 434 can includes openings or passages to allow for fluid to flow radially into an outer portion of the base part 430, which defines a further or second chamber 420. In some embodiments, as the flow is redirected vertically as a result of the presence of the base part 430, turbulence is created, which thus promotes mixing and homogeneity of the fluid throughout the bioreactor and thus enhances the cell culturing process.

Two intermediate parts 450a, 450b are shown as being stacked, with a peripheral connector (groove 454) of the first (lower) part 450a engaging a corresponding connector (tongue 452) of the second (upper) part 450b. As can be appreciated from FIG. 16, in some embodiments, each intermediate part 450a, 450b can include an outer side wall 456 supporting the tongue 452 and groove 454, respectively. In some embodiments, radially inwardly, an inner wall 458 carries inner and outer connectors, which may be in the form of upstanding ledges 460, 462, can be provided for receiving the corresponding ends of a tube 436, which thus forms periphery of the fifth or return chamber 428.

In some embodiments, the first or lower intermediate part 450a may also include openings, such as elongated arcuate slots 464, which at least partially receive connectors, of the base part 430, such as upstanding projections 434a from the wall 434. In some embodiments, an interior ledge 466 can form central openings 466a in the intermediate parts 450a, 450b for permitting fluid to flow in an inner column defined by the wall 434, as well as to receive any temperature sensor, dip tube or the like (which would be positioned after the fluid exits the fixed bed). In some embodiments, the second intermediate part 450b may be similarly constructed to promote interchangeability, in which case the openings (slots 464) in the second or upper intermediate part 450b allow for the creation of the thin falling flow or film of fluid within the fifth or return chamber 428, as previously noted.

In some embodiments, extending between the inner and outer walls 456, 458 are a plurality of supports 468. In some embodiments, the supports 468 include radially extending supports 468a and at least one circumferentially extending support 468b, which together can create a perforated or reticulated plate-like structure that allows fluid flow (which structure in this or any embodiment may comprise a screen, net, grid, or other skeletal structure, and may be rigid, semi-rigid, or flexible). In fact, the supports 468 may be designed to enhance fluid flow through the bed(s) by maximizing the amount of open space created by the openings for permitting fluid to pass. In some embodiments, for culturing cells, a fixed bed, such as the spiral bed (not shown) wound around wall 434 may be positioned in the chamber 424 formed between the parts 450a, 450b. In some embodiments, fluid passing from the upper intermediate part 450b can enters the fourth chamber 426 defined partially by cover part 470, and may flow to the column forming the fifth chamber 428 before returning to the first chamber 416 for recirculation.

In some embodiments, the cover part 470 includes a connector, such as tongue 472, for fitting into the corresponding connector (groove 454) of the second intermediate part 450b. In some embodiments, the cover part 470 can also include a first or central receiver, such as upstanding wall 474 for receiving a removable cap or lid 476, which may include various ports P for connecting with conduits for delivering fluids or other substances to the bioreactor 400 (and the fifth chamber 428). In some embodiments, the cap or lid 476 may also carry the temperature sensor or probe T, as shown, as well as other sensors, and may also be adapted for providing additions or removing substances from the bioreactor 400, or for regulating a product manufacturing process. As can be appreciated, in some embodiments, the cap or lid 476 can be well positioned to allow for sensing or fluid sampling to occur in connection with the return flow via chamber 428. In some embodiments, a second peripherally positioned receiver, such as upstanding wall 477, may also be adapted for connecting with a second cap or lid 478 for receiving sensors or depositing or withdrawing substances (including culture samples) from the bioreactor and, in particular, a peripheral portion thereof including the third chamber 426 in which cell culturing is completed. In some embodiments, the caps or lids 476, 478 may have different types of ports P and may be different sizes/shapes, or they may be identical to promote interchangeability.

By comparing FIG. 16 with FIG. 7, it can also be appreciated that the cap or lid 476, 478 may be used in connection with different sizes of bioreactors. Thus, in FIG. 16, it can be understood that the cap or lid 476, 478 has an outer diameter that is much less than an outer diameter of the bioreactor 400. In some embodiments, cap or lid 476, 478 could also be used with the bioreactor 300 of FIG. 7 (or any other), in which case the outer diameter would be about the same or perhaps even slightly greater than the diameter of the bioreactor 300.

In some embodiments, adhesives or glue may be used at the connections to hold the structures together. In some embodiments, threaded or locking (e.g., bayonet style) connections may also be used, such that a fluid-tight seal is maintained to prevent leakage and help ensure that sterility is maintained. In some embodiments, the arrangement of modular parts 430, 450, 470 allows for the bioreactor 400 to be pre-assembled, assembled or constructed on site rapidly, and potentially disassembled with similar rapidity. As it is possible to easily add additional tube(s) to form a heightened wall 434 or intermediate parts 450, the number of fixed beds or height of the bioreactor 400 may be adjusted to suit a particular need or process setting depending on the application.

In some embodiments, the flow from one fixed bed to the next-adjacent one in the chamber is direct or uninterrupted. In some embodiments, the outer chamber 424 for receiving the bed creates a continuous flow path through the multiple beds present therein, which may be structured fixed beds, unstructured fixed beds, or other beds. In some embodiments, the continuous and substantially unimpeded flow helps to promote homogeneity as if the modules are actually a single bed and thus improves the predictability and quality of the cell culturing process. Homogeneity means that the cell distribution throughout the bed is homogeneous or having a somewhat equal spread.

Figure 18:
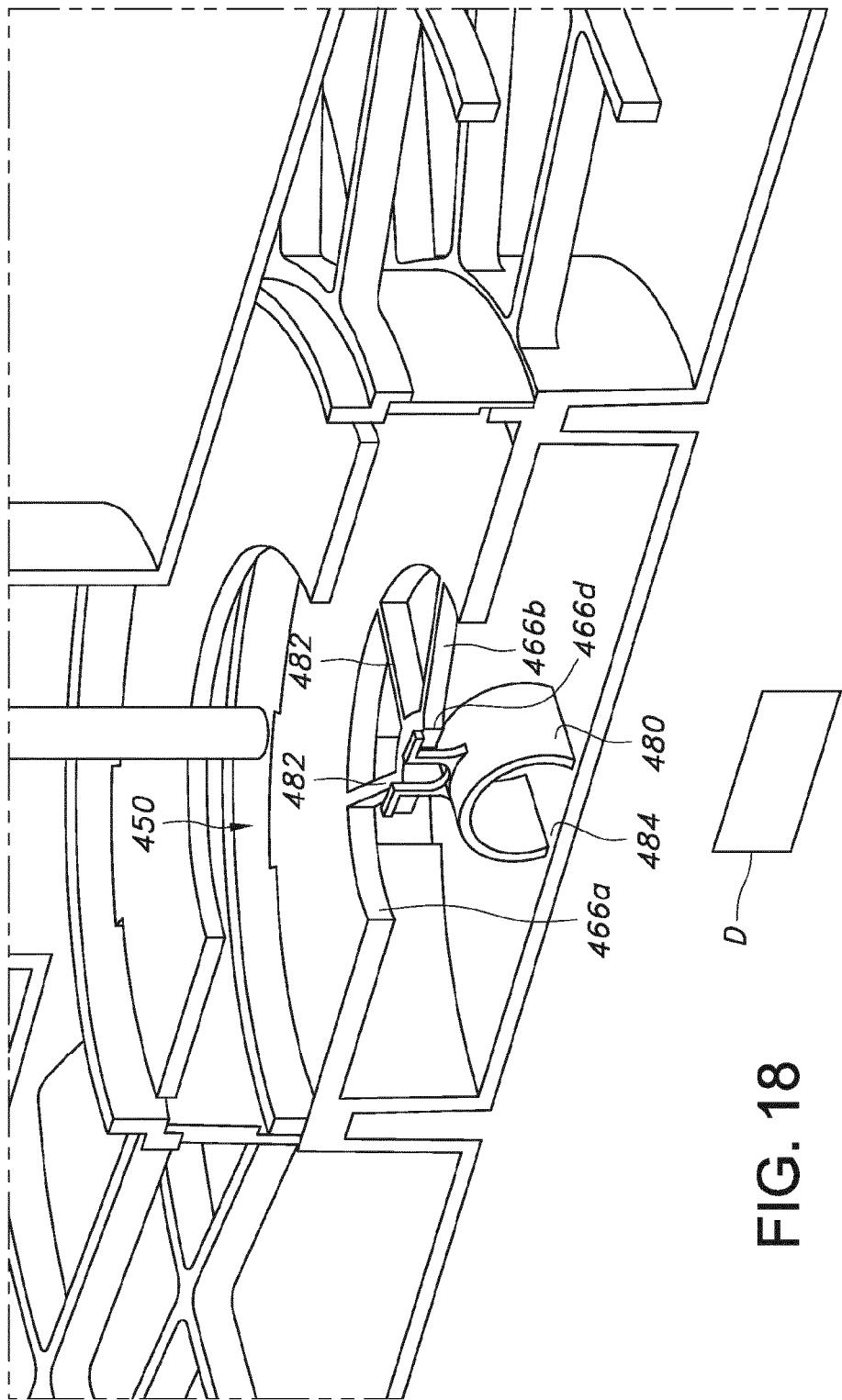
FIG. 18 is a partially cutaway view of portion of the bioreactor of FIG. 16.

FIG. 18 illustrates an alternative embodiment of an intermediate part 450, which can be adapted for positioning above the base part 430. In some embodiments, a plurality of radially extending supports 466b are provided in the central opening 466a, which connect with an interior connector in the form of a ring 466d. In some embodiments, the ring 466d may be sized to receive part of a carrier 480 for carrying the agitator (not shown), and thus suspending it above the floor of the base part 430. In some embodiments, based on the structure, friction and concomitant particle shedding as a result of frictional contact between the impeller and the floor of the base part 430 during rotation is avoided.

As illustrated, in some embodiments, the carrier 480 may comprise a pair of compressible clips 482, which may be squeezed together to pass through opening in the ring 466d, and then released to securely suspend the carrier from the intermediate part 450, while permitting relative movement that allows the carrier to rotate freely. In some embodiments, the carrier 480 may include a socket 484, shown as being C-shaped in cross section, that receives a corresponding portion of the agitator, such as impeller (not shown) or perhaps simply an elongated magnetic or ferromagnetic rod (not shown). In some embodiments, this portion may comprise an upwardly extending projection rotatably connected to the agitator by a bearing. As can be appreciated, in some embodiments, the socket 484 can allow for side-to-side movement of the agitator, as may be necessary to achieve alignment with a corresponding external or non-contact (e.g., magnetic) drive D located external to the bioreactor 400, such as below the base part 430.

Figure 18A:
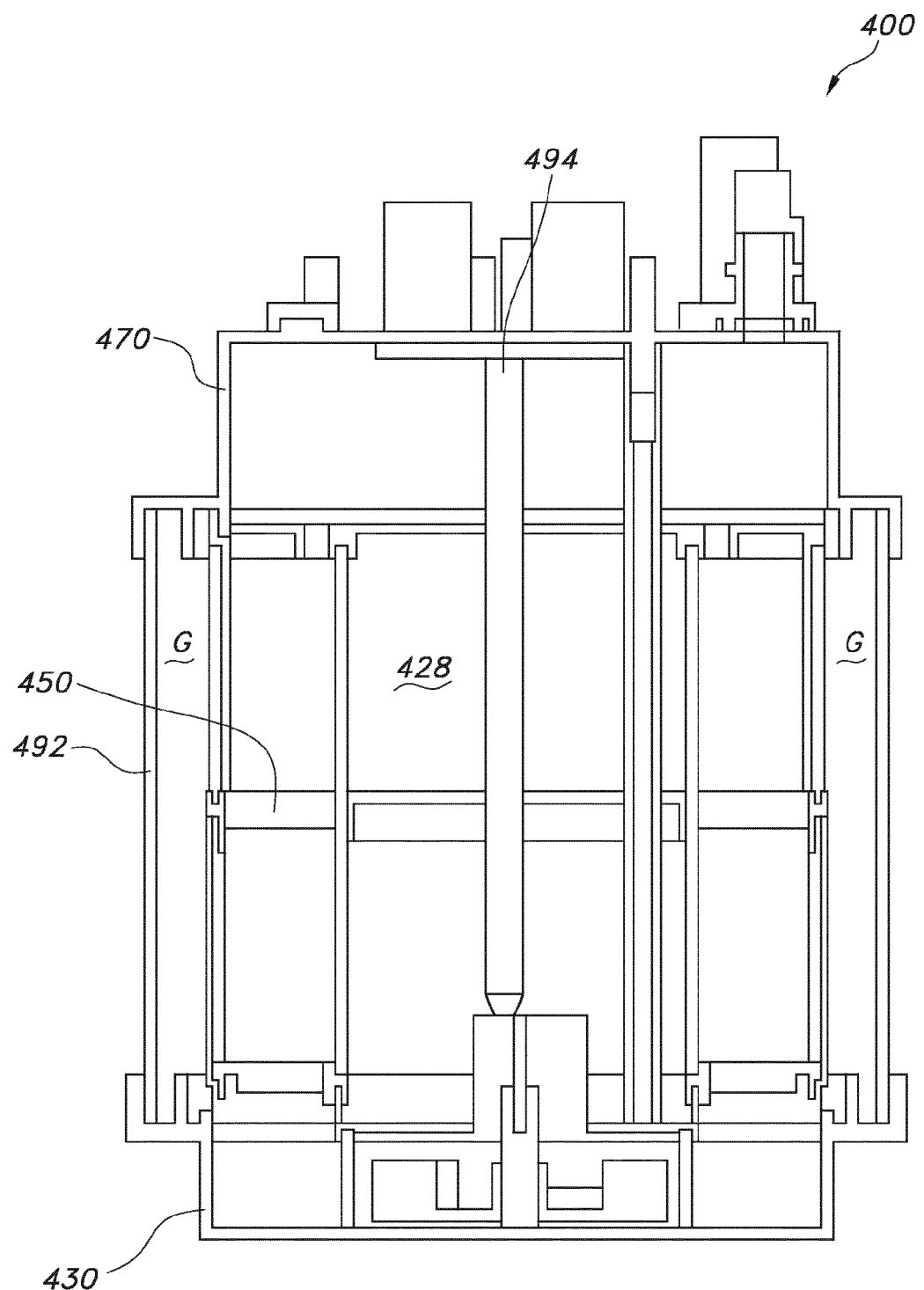
FIGS. 18A, 18B, and 18C are a cross-sectional views of further embodiments of the bioreactor of FIG. 16.
Figure 18B:
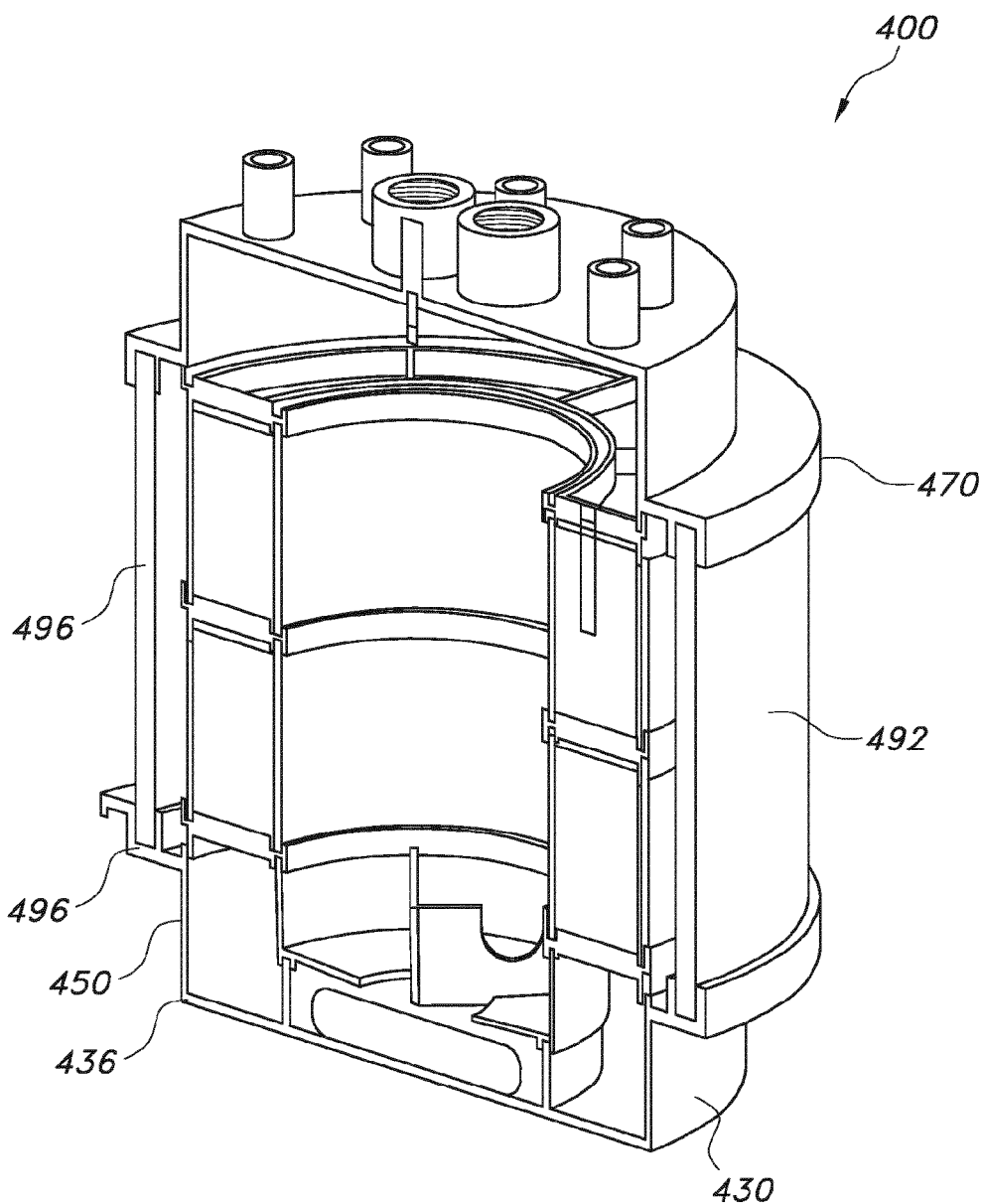

FIGS. 18A and 18B also illustrate an alternate embodiment of a modular bioreactor 400 including fixed beds 496. In some embodiments, the base part 430 and cover part 470 can be adapted for connecting with an outer casing 492, which creates a gap or space with the periphery of the intermediate parts 450. In some embodiments, the gap G or space may be used for providing a heating or cooling effect to control the temperature of the beds associated with the intermediate parts 450. The gap G or space may also simply supply insulation of the walls of the intermediate area of the bioreactor which are close to growing cells within the bed and likely to be sensitive to temperature variations. This insulation acts to prevent heat which is applied to the bottom of the base part 430 of the bioreactor from extending up to the adhered cells in the bed(s) 496.

FIG. 18A also illustrates the possible use of sparging in the bioreactor, which may be provided in any disclosed embodiment. In the illustrated arrangement, the sparging is provided by a sparger 494 located in the fifth chamber 428. The bubbles generated as a result may thus flow upwardly countercurrent to the return fluid flow.

These figures, and perhaps FIG. 18B best, also show that the intermediate parts 450 may engage internal tubes 436, which are fluid impervious to thus provide the chamber 428 for returning flow to the base part 430, where it may be agitated and returned to enter the beds from below and flow upwardly therethrough (in any embodiment disclosed). These tubes 436 may be provided such that one tube corresponds to each fixed bed 496 present, as shown, and two intermediate parts 450 engage each tube 436 (e.g., one from below and one from above). However, in this or any other disclosed embodiment, it should be appreciated that the innermost surface of the fixed bed, such as the innermost spiral wrap of a spiral bed, may be made to perform a similar function by making it or otherwise conditioning it so as to be impervious to fluid. For instance, the surface may be coated with a fluid-impervious or hydrophobic material, such that it still retains the fluid in the bed(s) and maintains a distinct, return flow of fluid through the central column formed by chamber 428.

Figure 18C:
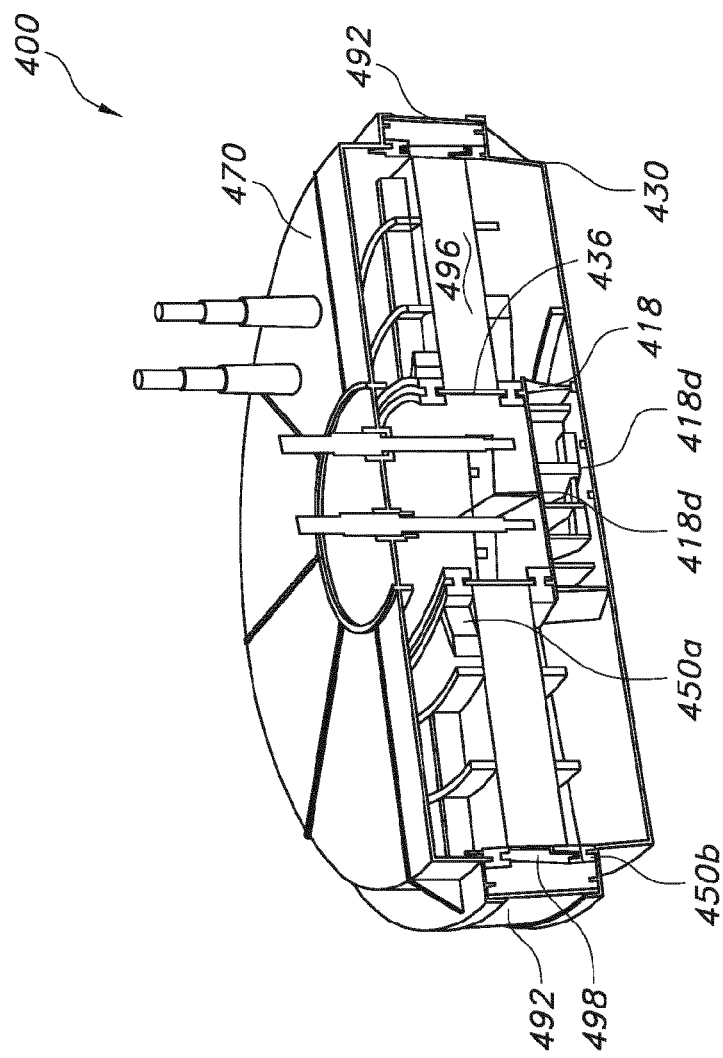

FIG. 18C also illustrates an embodiment of the bioreactor 400 including the intermediate parts 450a, 450b sandwiching a fixed bed 496, which may be a structured, spiral bed as previously illustrated and described. The base part 430 and cover part 470 are also provided and interface with the outer casing 492, creating an annulus or gap, which again may be insulated or associated with a heating or cooling means. In this or any other embodiment, the casing 492 may simply create a buffer or space (filled with air or other gas). This may allow for the temperature of the bioreactor 400 to be regulated more efficiently (e.g., quicker) and further allows it to be perfused and/or used in media recirculation with a lower requirement in term of media pre-heating.

This figure also illustrates the housing 418 for an agitator 418a. The housing 418 may be any one of the forms shown in FIG. 23, and thus may include a flow divider 418d. The inner partition in the form of tube 436 for partially forming the central column (i.e., return chamber 428 shown in FIG. 18A) is also shown. An outer partition is also shown, may also be in the nature of a cylindrical structure or tube 496 that removably interconnects with the parts 450a, 450b (and may be adhered in place using adhesives or other forms of bonding), but could also be a unitary structure with one or both of them.

Figure 19:
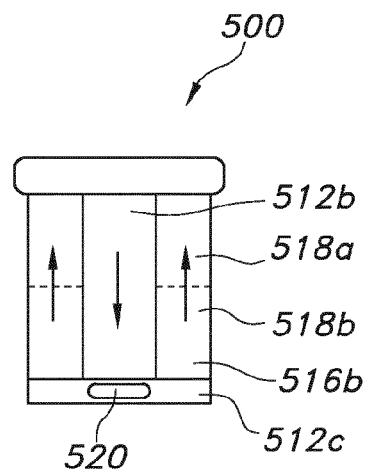
FIGS. 19 and 20 are schematic views of a fifth embodiment of a bioreactor according to the disclosure.
Figure 20:
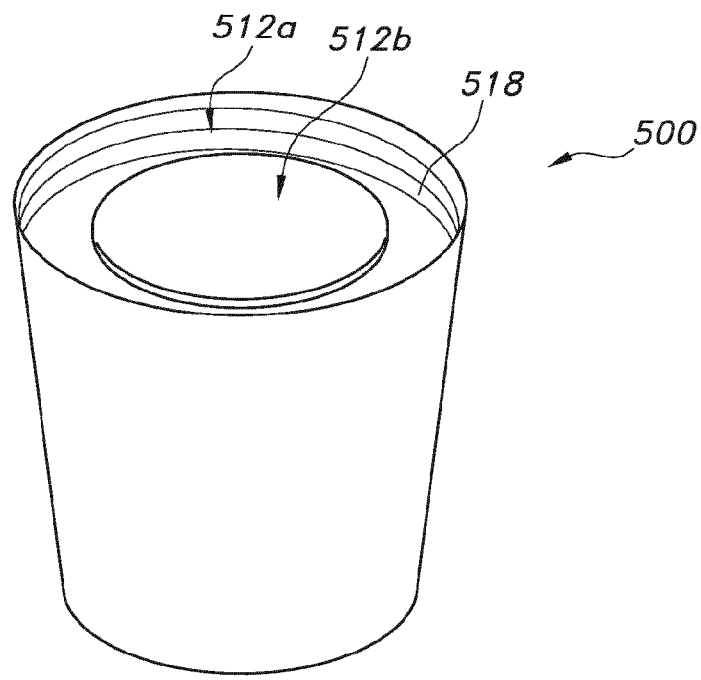

FIGS. 19 and 20 illustrate an example of a bioreactor 500 including one or more fixed beds, such as two vertically stacked, structured fixed beds 518a, 518b in the illustrated example. In some embodiments, the beds 518a, 518b can be arranged in an outer chamber 512a of the bioreactor 500 and may be the spiral beds shown in FIGS. 1-3. In some embodiments, an inner chamber 512b can also provide circulating fluid to or from the fixed bed(s). In some embodiments, the fluid may be caused to flow by an associated agitator, such as an impeller 520 located in a lower compartment 512c of the bioreactor 500. In some embodiments, the flow of fluids may be in a vertical direction within the fixed bed(s), such as from top to bottom or bottom to top. In some embodiments, the structured fixed bed(s) can be provided in the inner chamber 512b, with the outer chamber 512a serving to deliver fluid to and from the inner chamber.

Figure 21:
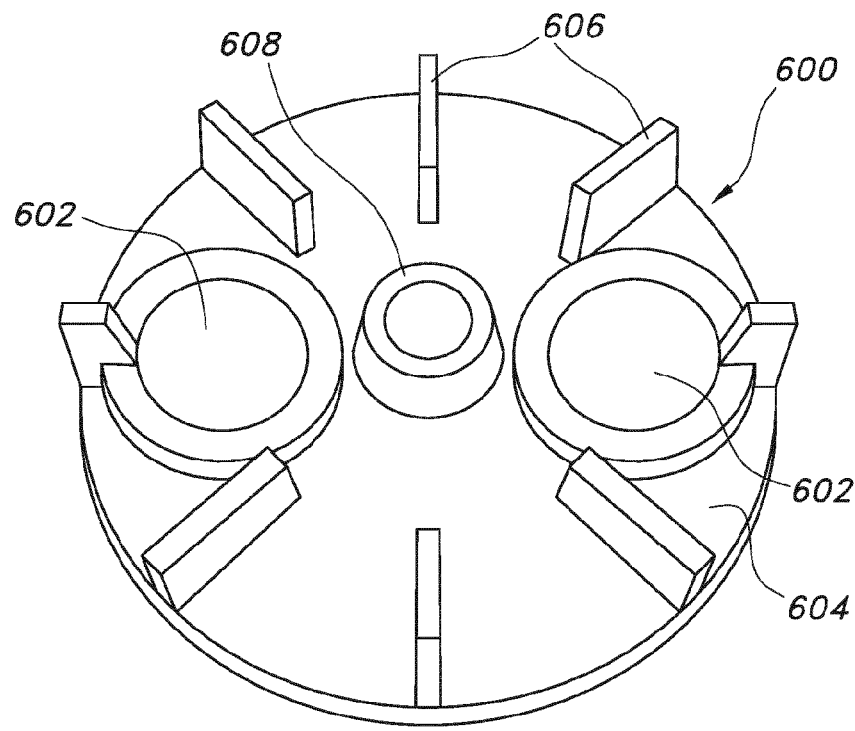
FIGS. 21 and 22 are bottom and top views of an embodiment of an impeller.
Figure 22:
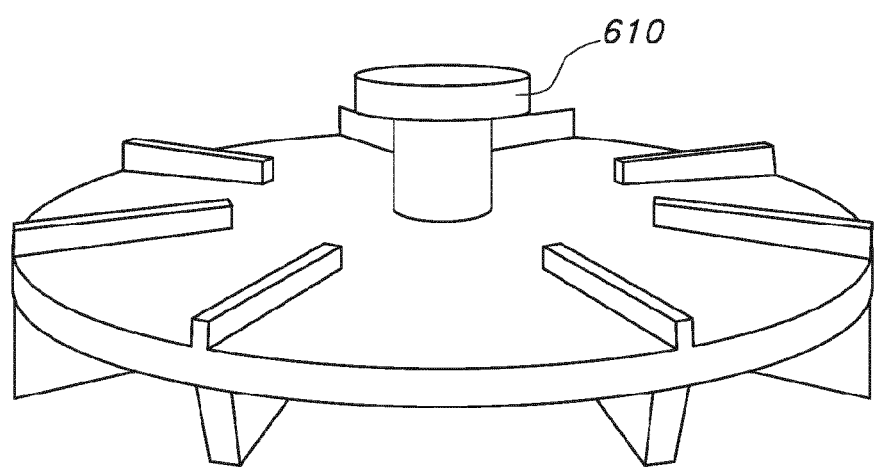

Referring now to FIGS. 21 and 22, in some embodiments, an agitator in the form of an impeller 600 can be used in any of the above described embodiments is shown. In some embodiments, the impeller 600 may comprise magnets 602 that can be inserted into a body 604 (machined or injected) having radially extending blades 606, and an opening 608, and through which a shaft 610 or other receiver can be inserted. In some embodiments, caps (not shown) may be provided over the magnets 602 to ensure that contact is not made with the culture media, and may be attached using an adhesive or threaded connection. In some embodiments, the magnets 602 can be overmoulded when the body 604 embodiment will be injected (injection molded). In some embodiments, it may also be possible to 3D print the embodiment, to pause the 3D printing, to insert the magnets, and to relaunch the 3D printing to form the impeller 600. In some embodiments, the impeller body 604 may be made in a durable, polymer material, such as polycarbonate or other suitable materials. In some embodiments, the impeller can be machined, injection molded, 3D printed, or fabricated in or other ways. The associated receiver or shaft 610 (if present) may be formed of polypropylene or other suitable materials, and may be machined, injected or 3D printed.

Figure 23:
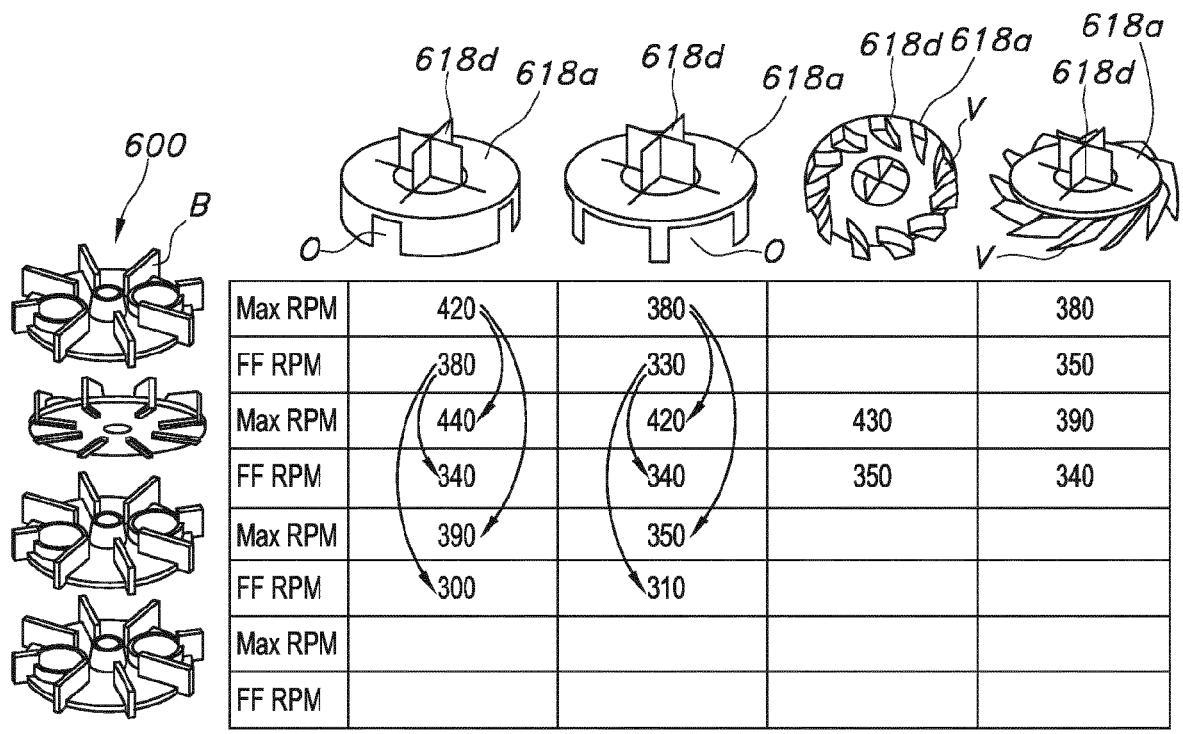
FIG. 23 is an illustration of various forms of impellers and associated housings.

FIG. 23 shows various combinations of impellers 600 with different containers 618a in a table form, with an indication of the relative efficiencies that result. In some embodiments, by adjusting the radial extent of the blades B and changing the number of outlets O in the container 618a to more than four (and possibly as many as 10-12), a higher efficiency in terms of fluid flow may be realized at a comparable rotational speed. In some embodiments, a divider, such as an upstanding wall 618d having an X-shaped cross-section may be provided adjacent to the inlet I of the container 618a for dividing the flow. In the two embodiments at the right of FIG. 21, it can also be understood that vanes V are providing for guiding the flow as it exits the container 618a and, as indicated, the vanes can have varying shapes or widths.

Figure 24:
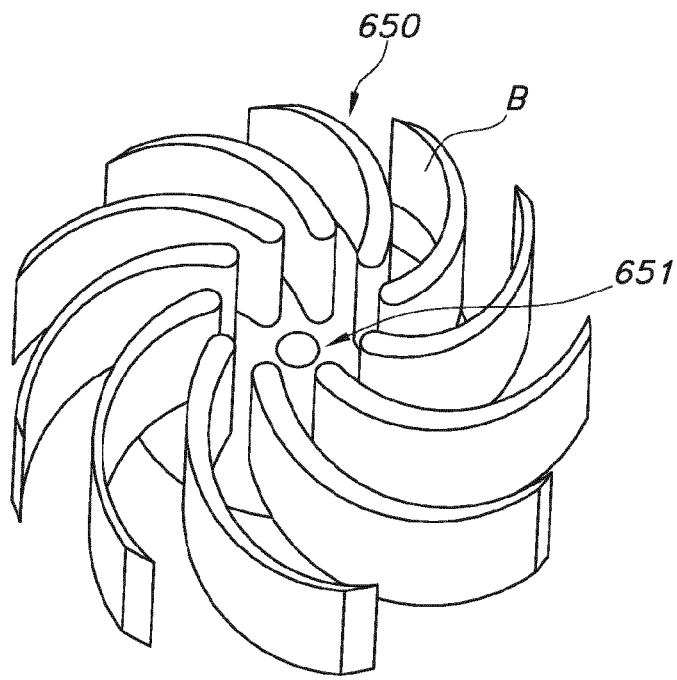
FIG. 24 is top view of another impeller according to the disclosure.

FIG. 24 further illustrates a further example of an impeller 650 having blades B that curve in a radial direction. In some embodiments, the impeller 650 may include a central space 651 for receiving flow from the inlet I of the container 618a when used in connection with such, and the blades B thus serve to redirect the fluid outwardly through the outlets O. The impeller 650 is shown as having 10 blades, but more or fewer may be provided as desired or necessary. In some embodiments, the impeller 650 may also include one or more magnets (not shown), as described above, for forming a non-contact coupling with an external drive (not shown). Because living cells are sensitive to mechanical forces such as shear, the impeller design needs to avoid shear while providing for efficient and optimized fluid flow. The impeller 650 achieves such complimentary goals.

Any of the components of the above bioreactors 100-500 may be made to be a single use or disposable component, or may be made to be reusable. Furthermore, the components used may be a mix or hybrid of disposable and reusable materials. In some embodiments, the bioreactor 100-500 may have a diameter of approximately 50-60 cm. In some embodiments, the bioreactor 100-500 may have a diameter or height of approximately more than about 5, 10, 15, 20, 25, 30, 35, 40, 45, 50, 60, 70, 80, 90 or 100 cm. In some embodiments, the cover part or lid 476, 478 that may be used in connection with bioreactor 400 may have a diameter of approximately more than 2, 4, 5, 6, 8, 10, 12, 15, 20, 25, 30 or 50 centimeters. In some embodiments, the intermediate parts 450*a*, 450*b* may have a height of approximately about 2.5-5.0 centimeters or more. In some embodiments, the overall bioreactor 400 may have a height of approximately 20-50 centimeters. In some embodiments, a bioreactor can comprise more than one fixed bed. In some embodiments, an impeller speed may be adjusted to compensate for an increase in pressure drop so as to maintain consistent linear velocity from bottom of reactor to top of reactor. In such case, shear stress on cells can be maintained constant for all sizes of bioreactor. In some embodiments, a sparger may also be provided. In some embodiments, it may be desirable during sparging to cease operation of the impeller to avoid transporting the air bubbles into the fixed bed.

In some embodiments, in the modular case, the bioreactor 100, 200, 300, 400, 500 may comprise any number of components for adjusting the relative height thereof. For example, a plurality of intermediate parts, such as parts 450, may be used to create an increased height. In some embodiments, the bioreactors 100, 200, 300, 400, 500 may also be provided in a number of different diameters, and each diameter may comprise one or more intermediate parts for creating different heights based on a particular application. In some embodiments, the fixed bed growth surfaces may range from <<1 m2 to 2 m2, 7-30 m2, 150-600 m2, >2,400 m2, and may vary among different sizes (height or diameter) of bioreactors. As noted, a plurality of fixed beds may be provided in a stacked configuration, such as one, two, three, four, or more fixed beds.

In some embodiments, the bioreactor described herein comprises a volume from about 100 mL to about 10 L. In some embodiments the bioreactor described herein comprises a volume from about 100 mL to about 5 L and a structured high-density growth surface of from about 5 m$^2$ to about 50 m$^2$. More preferably the bioreactor described herein comprises a volume from about 1 L to about 5 L. from about 10 m$^2$ to about 30 m$^2$.

In some embodiments, one or more of the bioreactor parts comprise polycarbonate. In some embodiments the one or more bioreactor parts comprise rigid polycarbonate. In some embodiments, the bioreactor vessel comprises polycarbonate. In some embodiments, one or more bioreactor parts are injection molded.

Figure 25:
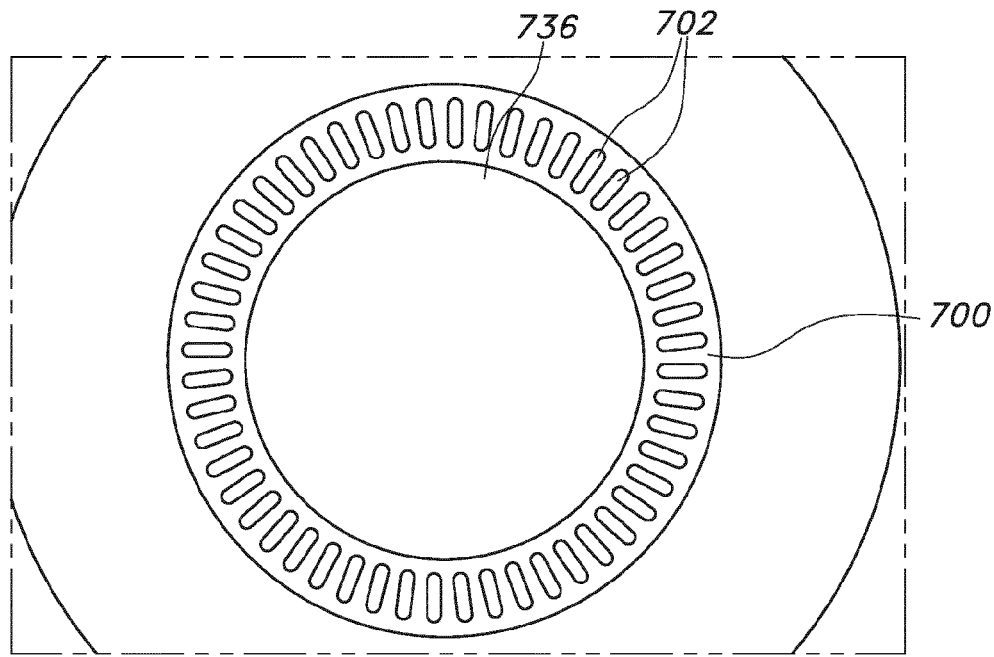
FIGS. 25 and 26 illustrate an embodiment of a flow disruptor.
Figure 26:
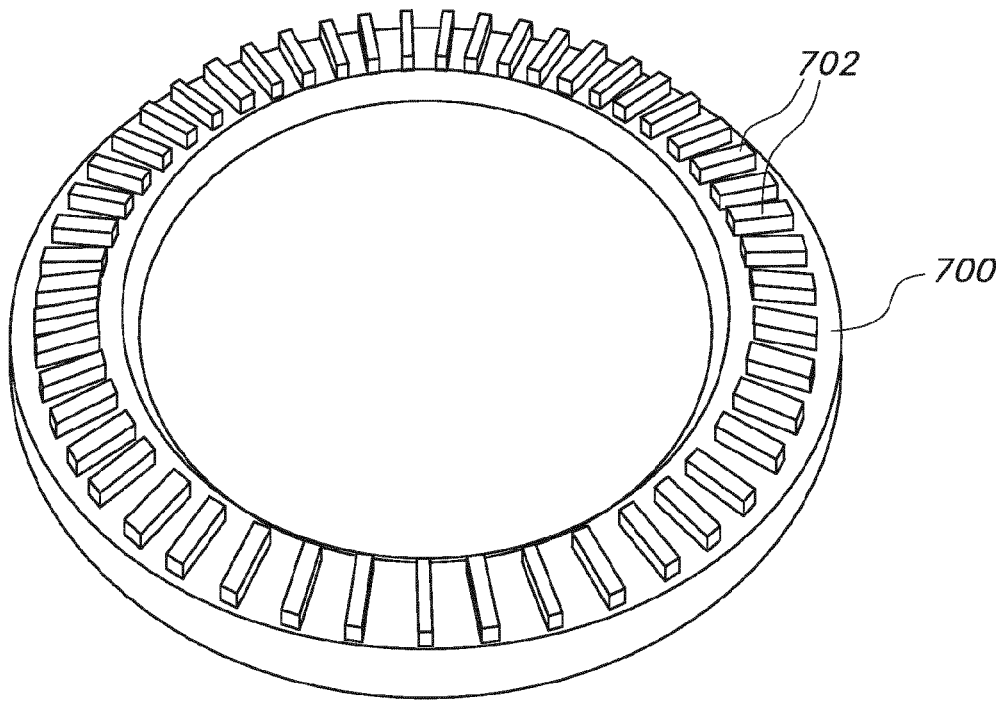

In some embodiments, in the above-described "waterfall" arrangements, it may be desirable to increase the oxygen transfer (or kLa, the volumetric mass-transfer coefficient that describes the efficiency with which oxygen can be delivered to a bioreactor for a given set of operating conditions) by providing a degree of turbulence as the fluid passes into the inner or central column. To achieve this result, one or more flow disruptors may be provided to interrupt the laminar flow and cause it to become turbulent. FIGS. 25 and 26 illustrate a further possible modification for the modular bioreactor, in which the flow disrupters or dividers may be provided as upstanding projections 702 on a ring 700 (thus forming a crown) which may be located above the central column. Consequently, fluid flow otherwise entering the central column 736 as a film may be "broken" by the projections 702, which thus form individual streams that are more turbulent and enable better oxygen transfer. In some embodiments, the projections 702 can break the potential swirling movement upon leaving the fixed bed, and ensure that the fluid flow can be aligned with the center of the bioreactor.

Figure 27:
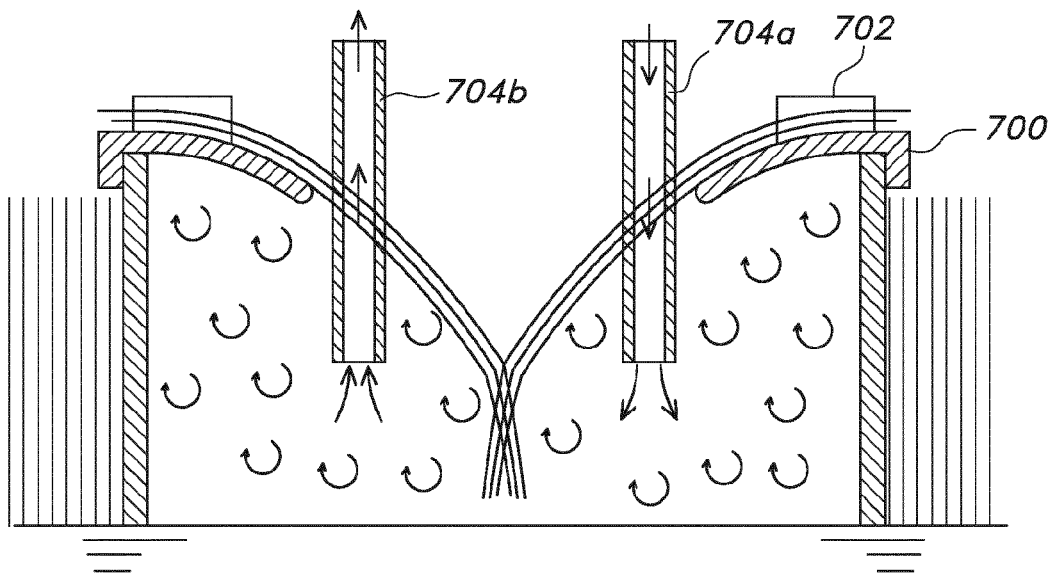
FIGS. 27 and 28 illustrate the use of conduits for supplying a gas to a portion below a "waterfall" of a bioreactor.
Figure 28:
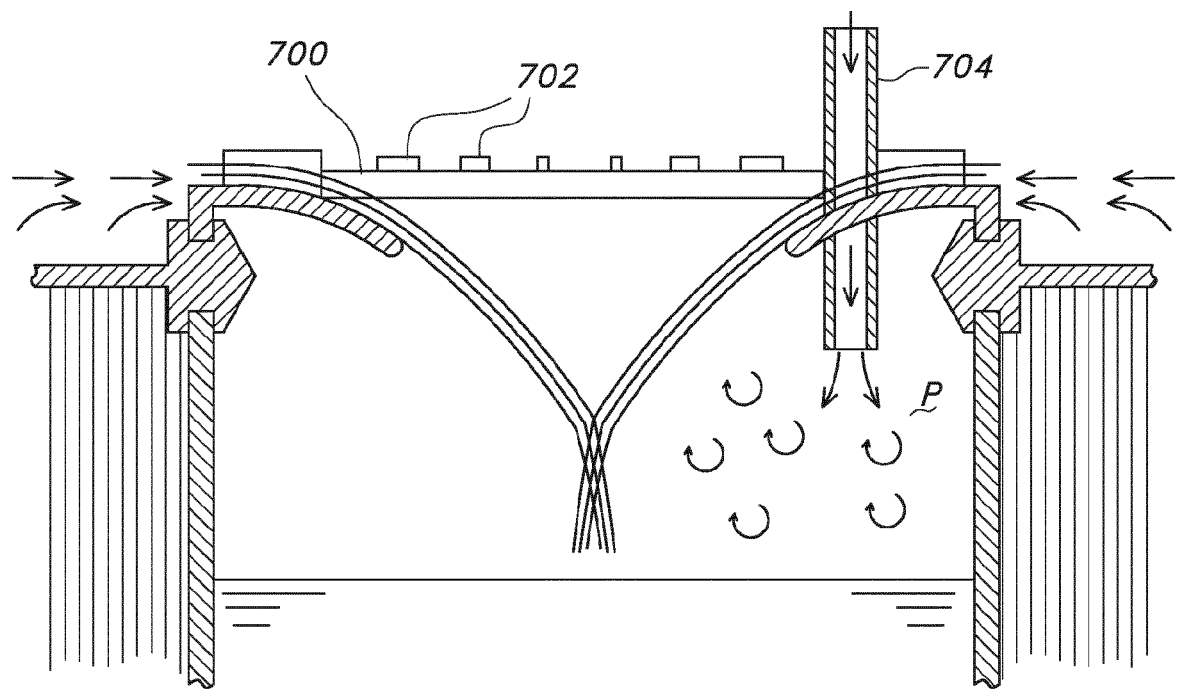

Turning to FIGS. 27 and 28, it can be understood that the resulting individual flows may ultimately recombine within the central column or columnar region formed by the inner wall of structured fixed bed, which may lead to added turbulence. Furthermore, it can be further understood that the ring 700 may cause the flow to assume a parabolic trajectory into the column, which can create a pocket P below the flow, where air/oxygen may become trapped. In some embodiments, to allow for gaseous exchange to occur between this pocket P and the interior of the bioreactor above the central column, one or more conduits 704 may be provided. In FIG. 27, a single conduit 704 is shown, which thus forms an inlet for gas flow. As shown in FIG. 27, multiple conduits 704*a*, 704*b* may be provided, and may serve as inlets and/or outlets for gas, such that it is renewed. As further indicated, the conduits 704 may be integral with the ring 700, as shown in FIG. 27, or may be separate from it, as shown in FIG. 28.

Figure 29:
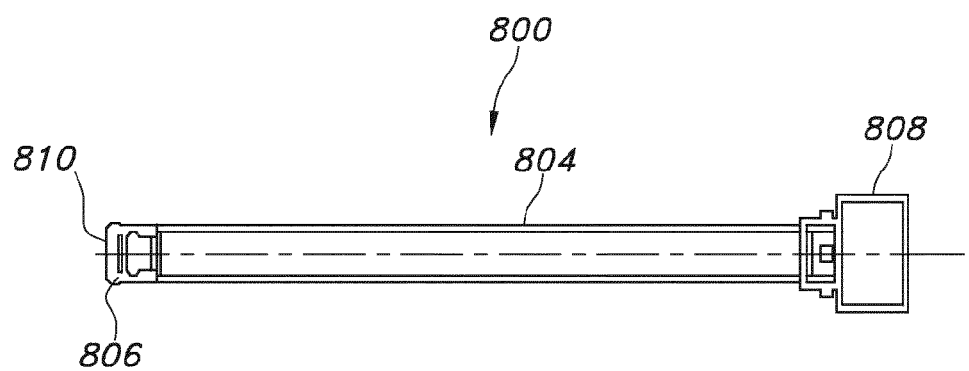
FIGS. 29 and 30 illustrate embodiments of a probe for use in connection with a bioreactor.
Figure 30:
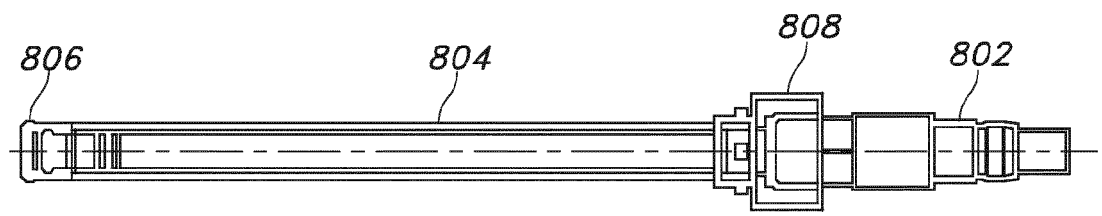

Turning now to FIGS. 29 and 30, a disposable (e.g., plastic or polymer) connector 800 for connecting a non-disposable (e.g., stainless steel) probe 802 for sensing various conditions of the bioreactor 100, 200, 300, 400, 500 is shown. In some embodiments, the connector 800 may comprise a tube or sleeve 804 associated with a cap or cover 806 at one end, and an adaptor 808 at the other, which may be for connecting with a port in any wall or portion of the bioreactor 100, 200, 300, 400, 500 such as by way of a threaded connection. In some embodiments, an optically transmissive portion, such as a membrane 810 attached to the cap 806, may be provided for interfacing with the probe 802.

The invention claimed is:
1. A system for producing biomolecules comprising:
a docking station;
a fixed-bed bioreactor comprising
   a first chamber comprising a structured fixed bed for entrapping cells therein, the first chamber having a fluid input end and a fluid output end; and
   a second chamber within the first chamber, the second chamber defined by an imperforate wall between the first chamber and the second chamber for returning fluid having passed through the structured fixed bed from the fluid input end to the fluid output end, back to the fluid input end of the first chamber;
a concentrator;
an intermediate vessel, positioned between said bioreactor and concentrator, wherein said intermediate vessel and concentrator are connected by a retentate conduit, allowing recirculating of liquid from an output of the concentrator to an input of said intermediate vessel; and
a controller, integrated in said docking station, which is able to control production and purification of the biomolecules; and
wherein the docking station is sized to be operated within a laminar flow cabinet or biosafety cabinet.
2. System according to claim 1, wherein said controller controls and operates bioreactor and process flow parameters and monitors and records data from one or more sensors present in said system.
3. System according to claim 2, wherein said sensors are one or more sensors chosen from pH sensors, temperature sensors, (dissolved) oxygen sensors or liquid level sensors.

4. System according to claim 1, wherein said bioreactor and concentrator is operated, monitored and controlled by said controller.

5. System according to claim 1, wherein said controller may be automated or manually operated.

6. System according to claim 1, wherein said docking station is formed by the casing of said controller.

7. System according to claim 1, wherein the system is fitted with at least one pump for allowing liquid flow into the bioreactor and at least one pump for allowing liquid flow out of the bioreactor.

8. System according to claim 1, wherein the system is fitted with at least one pump for base addition, wherein the pump operates both forward and backwards.

9. System according to claim 1, wherein said bioreactor and intermediate vessel are connected by a conduit, facilitating liquid transport from said bioreactor to said intermediate vessel and wherein said intermediate vessel and said concentrator are connected by a conduit facilitating liquid transport from said intermediate vessel to said concentrator.

10. System according to claim 1, wherein the system is fitted with a pump to provide cross-flow through said concentrator.

11. System according to claim 1, wherein said bioreactor is a perfusion bioreactor.

12. System according to claim 1, wherein said bioreactor is a fixed-bed perfusion bioreactor.

13. System according to claim 1, wherein the structured fixed bed extending spirally around the imperforate wall.

14. System according to claim 1, wherein said bioreactor is fitted with an agitator.

15. System according to claim 9, wherein said conduits are fitted with one or more pumps to provide cross-flow of said liquid through said concentrator.

16. System according to claim 1, wherein said concentrator is an ultra- or microfiltration device.

17. System according to claim 1, wherein said concentrator is a tangential flow filtration device.

18. System according to claim 1, wherein the system further comprises a decontamination vessel.

19. The system according to claim 1, wherein the structured fixed bed comprises a plurality of layers of material wound around the imperforate wall.

* * * * *